United States Patent
Vallone et al.

(10) Patent No.: US 6,929,923 B2
(45) Date of Patent: Aug. 16, 2005

(54) MODULATORS OF LEUKOCYTE ACTIVATION, BIC COMPOSITIONS AND METHODS OF USE

(75) Inventors: Marcy K. Vallone, San Francisco, CA (US); Brian R. Wong, Los Altos, CA (US); Esteban Masuda, Menlo Park, CA (US); Mark Powell, Burlingame, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 271 days.

(21) Appl. No.: 10/202,480

(22) Filed: Jul. 23, 2002

(65) Prior Publication Data

US 2004/0018566 A1 Jan. 29, 2004

(51) Int. Cl.[7] ................................................. C12Q 1/02
(52) U.S. Cl. ........................................ 435/7.24; 435/29
(58) Field of Search ................................ 435/7.24, 29

(56) References Cited

U.S. PATENT DOCUMENTS

| 6,696,267 B2 * | 2/2004 | Normant et al. ............... 435/29 |
| 2003/0171275 A1 * | 9/2003 | Baughn et al. ............... 514/12 |

FOREIGN PATENT DOCUMENTS

| WO | WO 98/21332 | * | 5/1998 |
| WO | WO 01/19988 | * | 3/2001 |
| WO | WO 01/46258 A2 | | 6/2001 |

OTHER PUBLICATIONS

Genbank Accession No. BC009731, http://www.ncbi.nlm.nih.gov/entrez/query.fcgi?cmd=Retrieve&db=nucleotide&list_ulds=16307282&dop . . .

* cited by examiner

Primary Examiner—David Saunders
(74) Attorney, Agent, or Firm—Townsend and Townsend and Crew LLP

(57) ABSTRACT

The present invention provides compositions and methods for modulating leukocyte activation. Nucleic acids encoding proteins and proteins so encoded which are capable of modulating leukocyte activation are provided. Compositions and methods for the treatment of disorders related to leukocyte dysfunction or dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

20 Claims, 11 Drawing Sheets

```
1    gcggtgaccg cgggcgggtg gggcgccggg tgaagaaacc aagacgcaga gaggccaagc
61   cccttgcctt gggtcacaca gccaaggag  gcagagccag aactcacaac cagatccaga
121  ggcaacaggg acatggccac ctgggacgaa aaggcagtca cccgcagggc caaggtggct
181  cccgctgaga ggatgagcaa gttcttaagg cacttcacgg tcgtgggaga cgactaccat
241  gcctggaaca tcaactacaa gaaatgggag aatgaagagg aggaggagga ggaggagcag
301  ccaccaccca caccagtctc aggcgaggaa ggcagagctg cagcccctga cgttgcccct
361  gccctggcc  ccgcacccag ggcccccctt gacttcaggg gcatgttgag gaaactgttc
421  agctcccaca ggtttcaggt catcatcatc tgcttggtgg ttctggatgc cctcctggtg
481  cttgctgagc tcatcctgga cctgaagatc atccagcccg acaagaataa ctatgctgcc
541  atggtattcc actacatgag catcaccatc ttggtctttt ttatgatgga gatcatcttt
601  aaattatttg tcttccgcct ggagttcttt caccacaagt ttgagatcct ggatgccgtc
661  gtggtggtgg tctcattcat cctcgacatt gtcctcctgt tccaggagca ccagtttgag
721  gctctgggcc tgctgattct gctccggctg tggcgggtgg cccggatcat caatgggatt
781  atcatctcag ttaagacacg ttcagaacgg caactcttaa ggttaaaaca gatgaatgta
841  caattggccg ccaagattca acaccttgag ttcagctgct ctgagaagga caagaaatt
901  gaaagactta caaactatt  gcgacagcat ggacttcttg gtgaagtgaa ctagacccgg
961  accagctccc ctcaaaaaga agacactgtc tcatgggcct gtgctgtcac gagaggaaca
1021 gctgcccctc ctgggccgct tggtgagagg tttggtttga tacctctgcc tccctcctgc
1081 cagcatggat tctgggtgga cacagccttg tggaaggtcc agtaccacca agagctgccc
1141 atccactccc accccacact gtatcaaatg tatcacattt tctcatgttg aacactttag
1201 ccttaattga aaatgagcaa caaagctgga caattgctag ttgtatataa aatttaatct
1261 caccgaatgt acagttttca aatttcacgt gtatattaag gaactgatgc atctgagcat
1321 tctgaaagaa agaaaaagaa gctactttag ctgccacccc attctagaaa agtctcttat
1381 tttcaagctg ttctaaatag cttcgtctca gtttccccaa aaggggtacc caggcccctc
1441 ctctgtgtgc cccagctgca tcagccagct tctaggtggc tccattgttt tctgccacct
1501 gacaacattt ttcctcaatt actgtacaac tactgtataa aataaaacaa ctactgtata
1561 aaataaactc tctcttttcc ctggaaaaaa aaaaaaaaaa aaaaaaaaaa aaaaaaaaaa
1621 aaaaaaaaaa aaaaaaaaaa aaaaaaaaaa
```

Human BIC, cds 133-954

FIG.\_1

```
1    matwdekavt rrakvapaer mskflrhftv vgddyhawni nykkweneee eeeeeqpppt
61   pvsgeegraa apdvapapgp aprapldfrg mlrklfsshr fqviiiclvv ldallvlael
121  ildlkiiqpd knnyaamvfh ymsitilvff mmeiifklfv frleffhhkf eildavvvvv
181  sfildivllf qehqfealgl lilrlwrva  riingiiisv ktrserqllr lkqmnvqlaa
241  kiqhlefscs ekeqeierln kllrqhgllg evn
```

Human BIC protein, 273 aa

FIG.\_2A

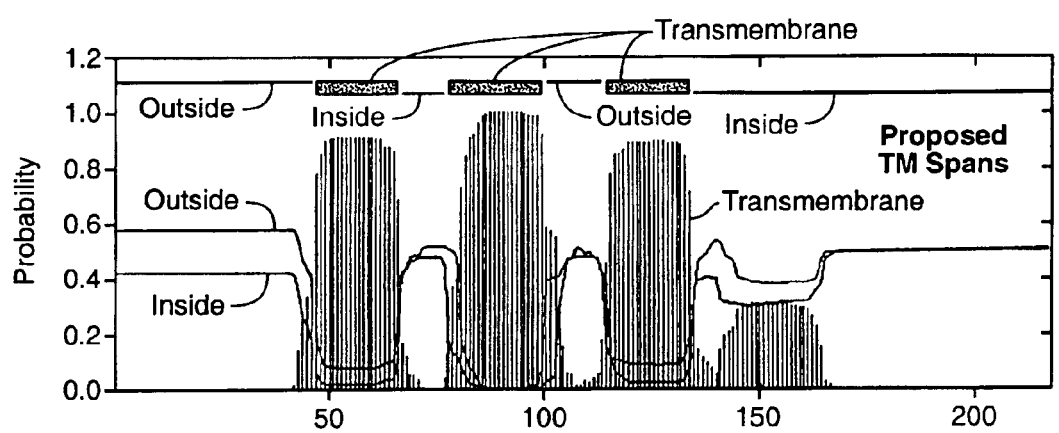
FIG._2B

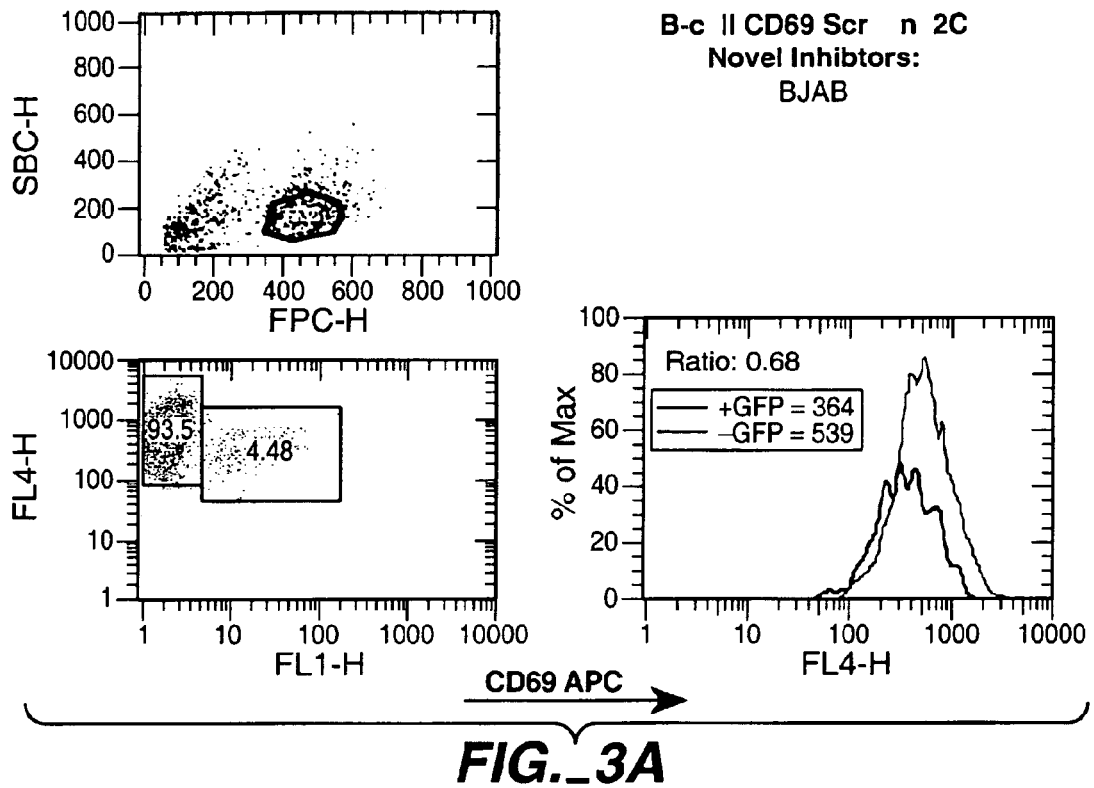
FIG._3A
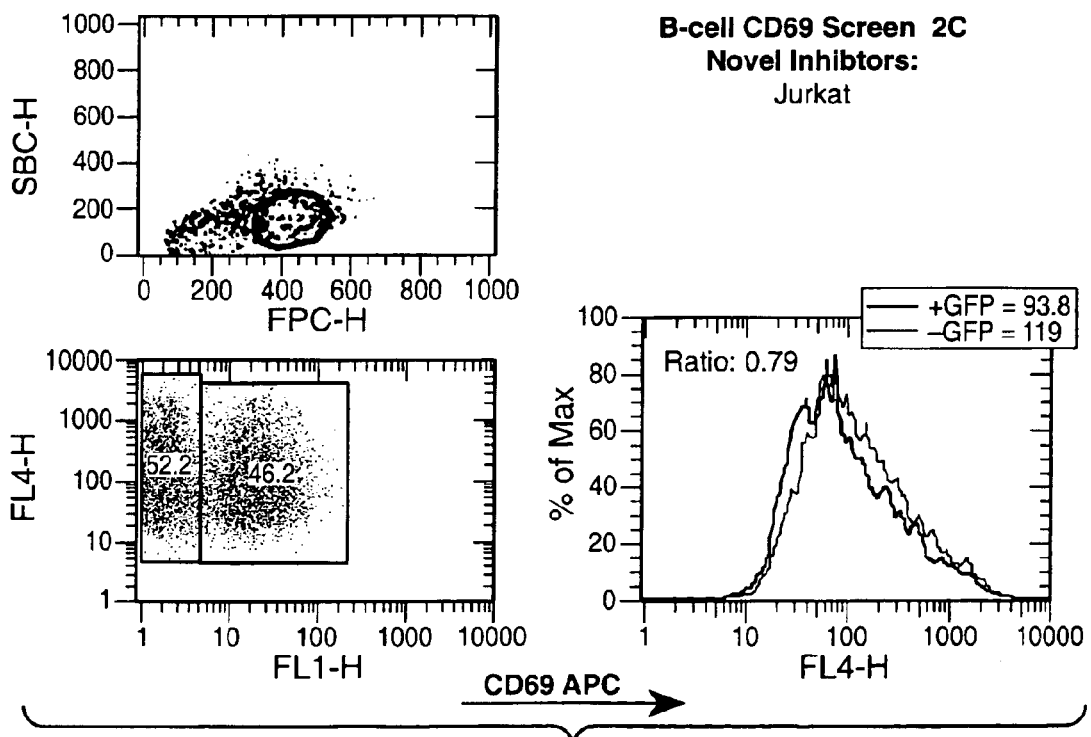
FIG._3B

TABLE 1

Human Autoimmune Diseases

| Disease | Self-Antigen | Immune Response |
|---|---|---|
| *Organ-Specific Autoimmune Disease* | | |
| Addison's disease | Adrenal cells | Autoantibodies |
| Autoimmune hemolytic anemia | Red blood cells | Autoantibodies |
| Goodpasture's disease | Renal and lung membranes | Autoantibodies |
| Graves' disease | Thyroid-stimulating hormone receptor | Autoantibodies |
| Hashimoto's thyroiditis | Thyroid proteins | $T_{DTH}$ cells, autoantibodies |
| Idiopathic thrombocytopenia | Platelet membranes | Autoantibodies |
| Insulin-dependent diatetes mellitus (IDDM) | Pancreatic beta cells | $T_{DTH}$ cells, autoantibodies |
| Myasthenia gravis | Acetylcholine receptors | Autoantibodies |
| Myocardial infarction | Heart muscle | Autoantibodies |
| Pernicious anemia | Gastric intrinsic factor | Autoantibodies |
| Poststreptococcal glomerulonephritis | Kidney | Immune complexes |
| Spontaneous infertility | Sperm | Autoantibodies |
| *Systemic Autoimmune Disease* | | |
| Ankylosing spondylitis | Vertebrae | Immune complexes |
| Multiple sclerosis | Brain or white matter | $T_{DTH}$ and $T_c$ cells, autoantibodies |
| Rheumatoid arthritis | Connective tissue | Autoantibodies, immune complexes |
| Scleroderma | Nuclei, heart, lungs, GI tract, Kidney | Autoantibodies |
| Sjogren's syndrome | Salivary gland, liver, kidney, thyroid | Autoantibodies |
| Systemic lupus erythematosus (SLE) | DNA, nuclear protein, RBC and platelet membranes | Autoantibodies, immune complexes |

*FIG._4*

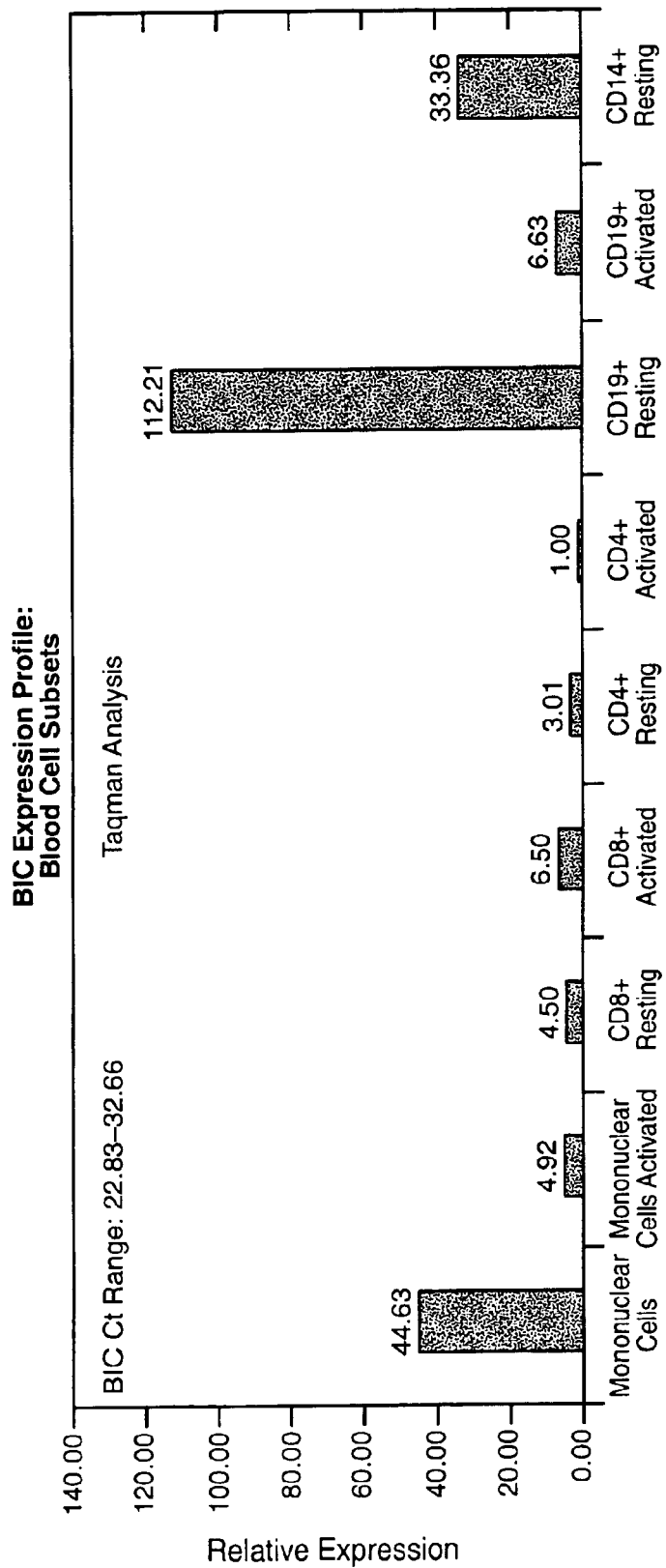
FIG._5A
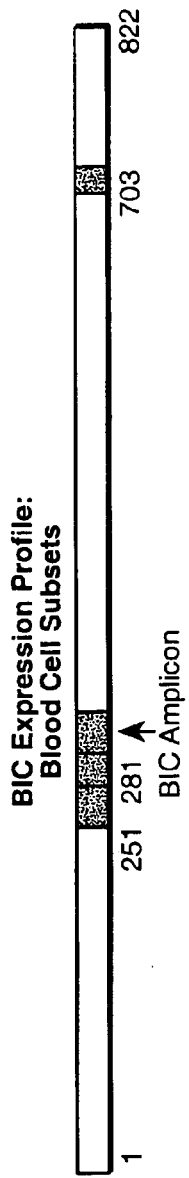
FIG._5B

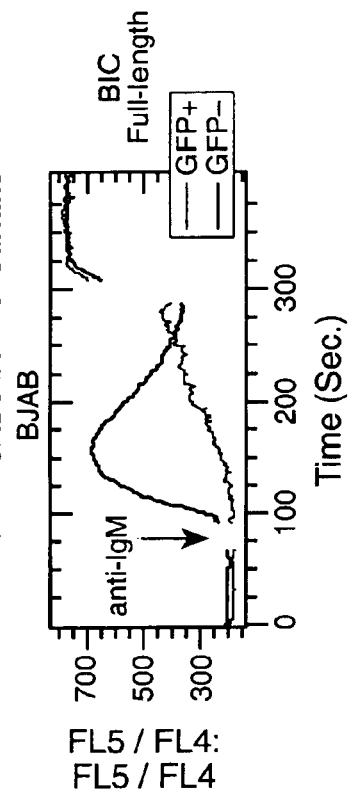
FIG._6A
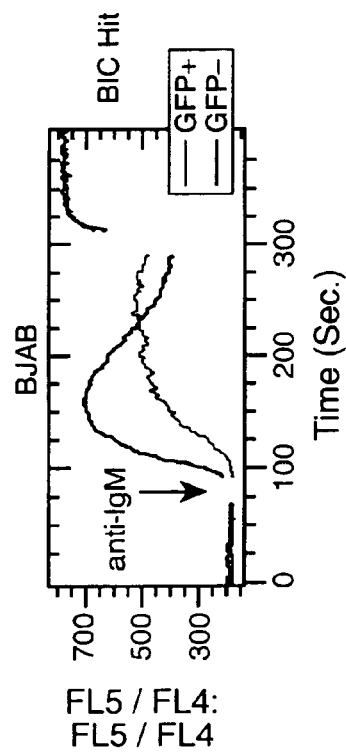
FIG._6B
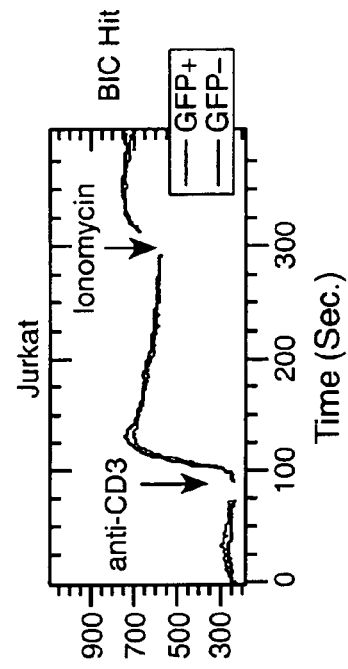
FIG._6C
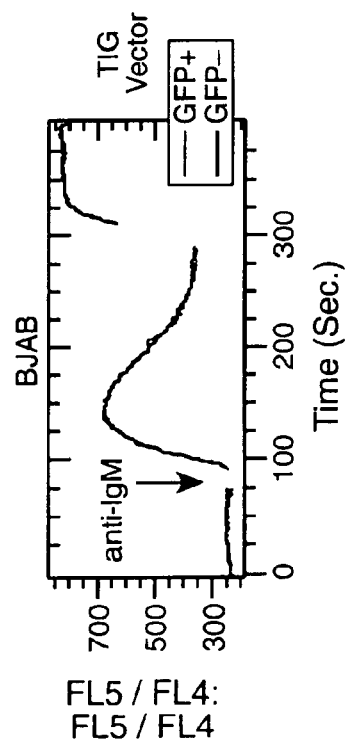
FIG._6D

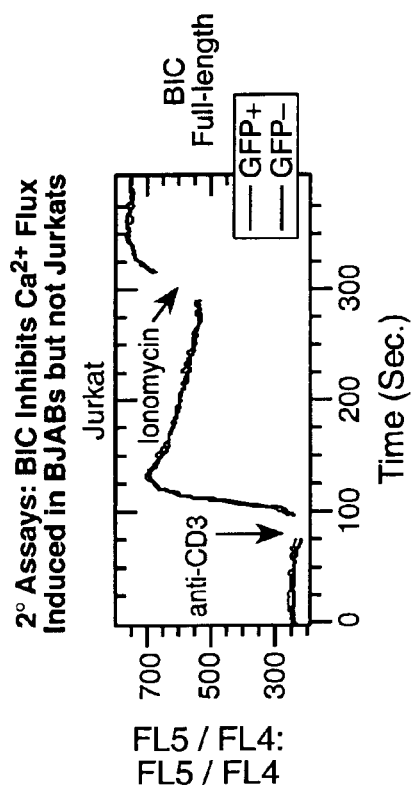
FIG._6E
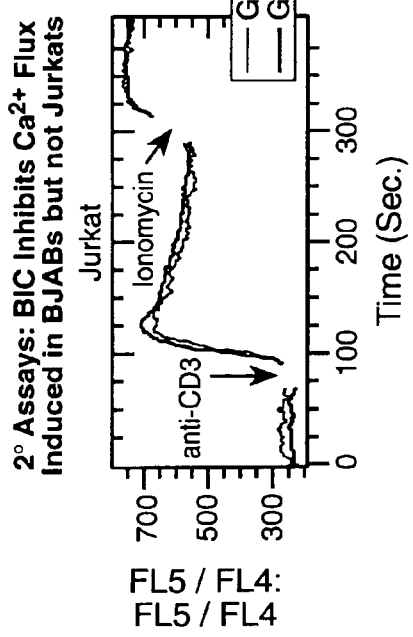
FIG._6F

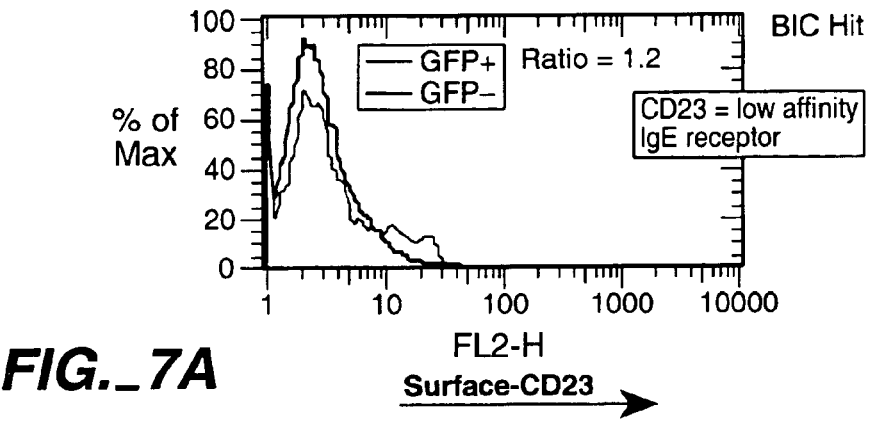
FIG._7A
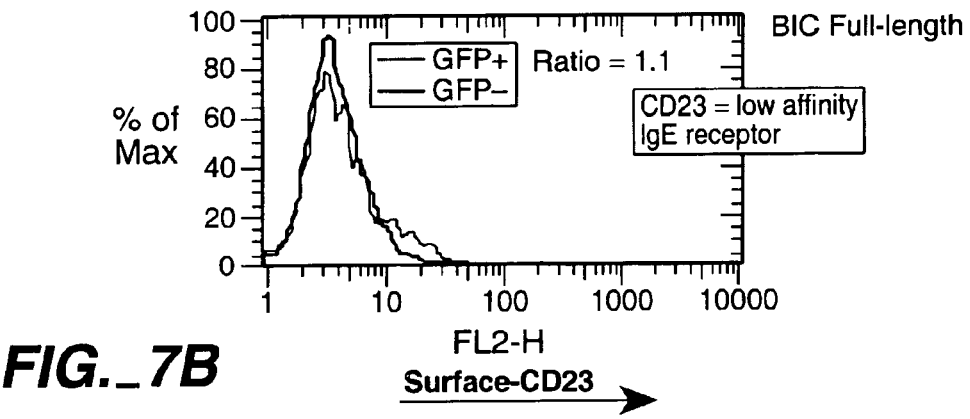
FIG._7B
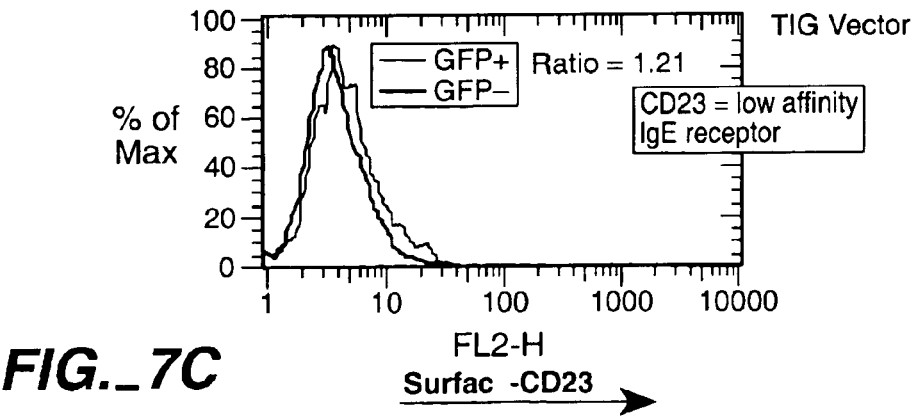
FIG._7C

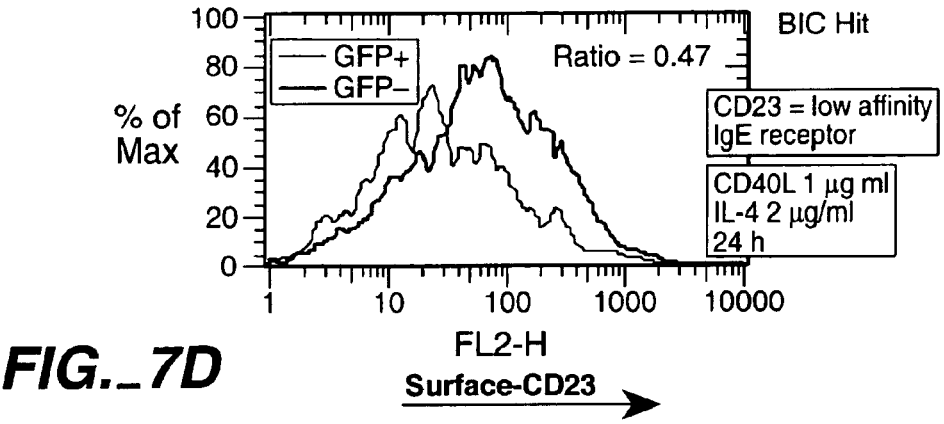
FIG._7D
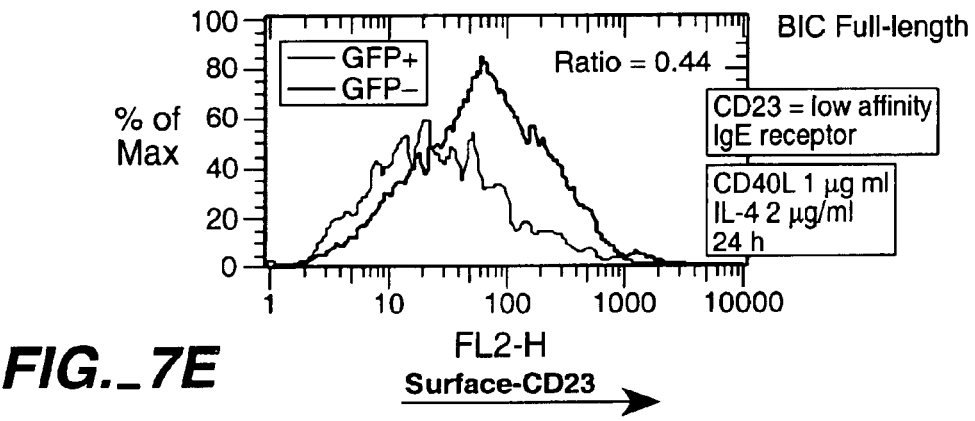
FIG._7E
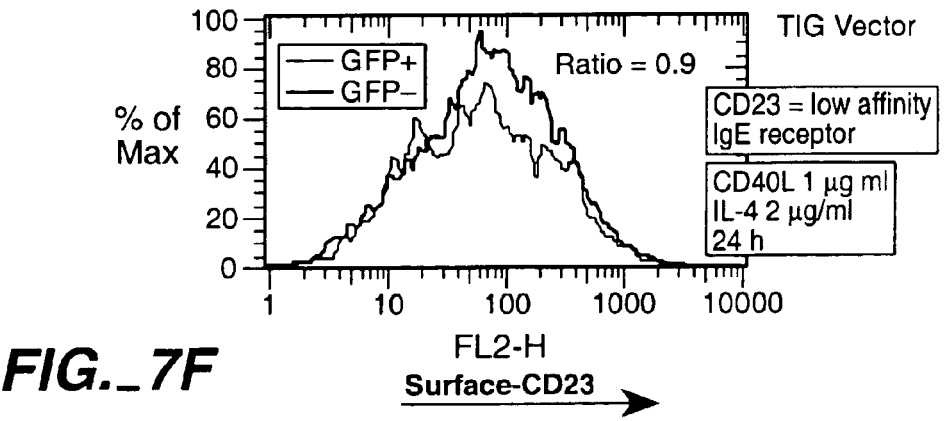
FIG._7F

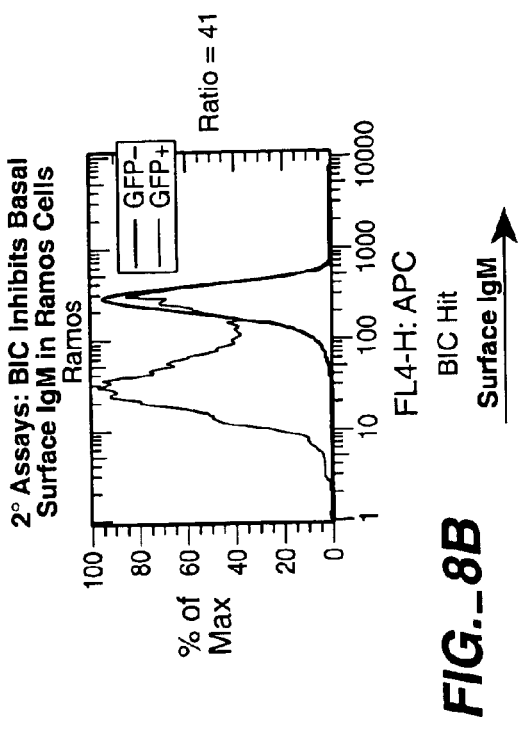
*FIG._8A*
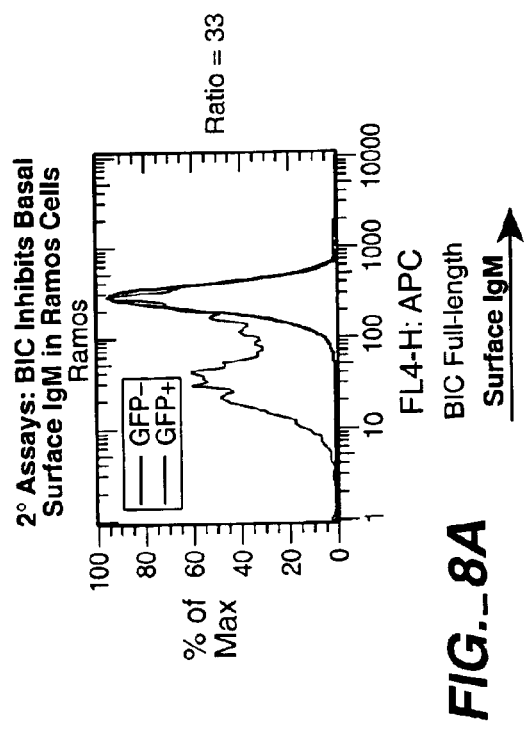
*FIG._8B*
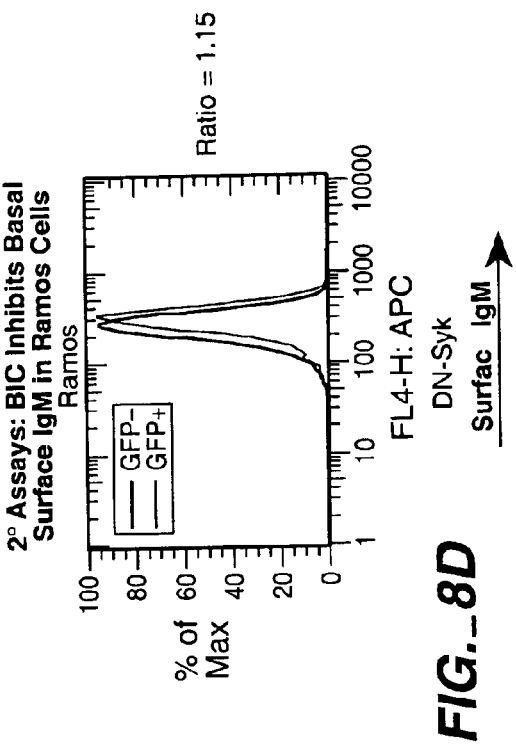
*FIG._8C*
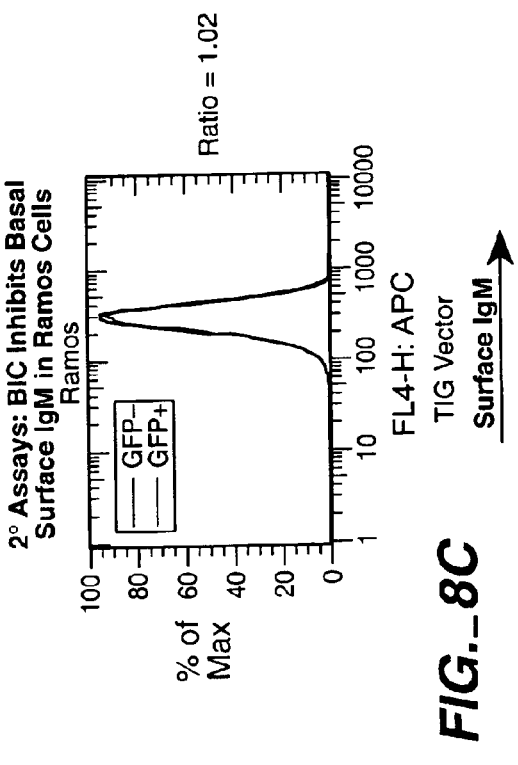
*FIG._8D*

```
   1    ctcagactac aggtgtgagc caccatgccc ggccttctcc tttaagtatt gttggcctca
  61    ctttcccaac taaaatggga gctcactaag aacaaaggct gttccttcat cttatactta
 121    gtaccttgaa agggcctacc acacagtagg tggtcacgtg ttagtctgtt aggtcttttg
 181    gattttctag gtagacaatc acatcgattg caaataatag tctttctctt ttcagtcttt
 241    gtatttcttt tttcttgttt tattgcattg actgagctca tcagtgaaat gttgaatagt
 301    agcaatgatg gagggcaccc caatcttatt atgctcaata ctcattaatt tatgcaatag
 361    gaatgtaaag tacctactgc aggtcaaatc ctgtgcctgg ggataacagt gtaacacatt
 421    tgagatcttt tcctgtccac tgaaatgcct gagcagtagc agtatttcag taaacacgac
 481    aatgctgaga atatcaccaa attctccaga cttgctgaag tgttcctttg ggatcctggt
 541    tcccaaaaag tatggacata ggtccctgct ggtggcccca ggttccaggc atcagtaag
 601    gttgggggct gcagactgga ccactgcacc gtggagcaga ggtgaagaaa ccaagacgca
 661    gagaggccaa gcccttgcc ttgggtcaca cagccaaagg aggcagagcc agaactcaca
 721    accagatcca gaggcaacag ggacatggcc acctgggacg aaaaggcagt cacccgcagg
 781    gccaaggtgg ctcccgctga gaggatgagc aagttcttaa ggcacttcac ggtcgtggga
 841    gacgactacc atgcctgaa catcaactac aagaaatggg agaatgaaga ggaggaggag
 901    gaggaggagc agccaccacc cacaccagtc tcaggcgagg tcatcatcat ctgcttggtg
 961    gttctggatg ccctcctggt gcttgctgag ctcatcctgg acctgaagat catccagccc
1021    gacaagaata actatgctgc catggtattc cactacatga gcatcaccat cttggtcttt
1081    tttatgatgg agatcatctt taaattattt gtcttccgcc tggagttctt tcaccacaag
1141    tttgagatcc tggatgccgt cgtggtggtg gtctcattca tcctcgacat tgtcctcctg
1201    ttccaggagc accagtttga ggctctgggc ctgctgattc tgctccggct gtggcgggtg
1261    gcccggatca tcaatgggat tatcatctca gttaagacac gttcagaacg gcaactctta
1321    aggttaaaac agatgaatgt acaattggcc gccaagattc aacaccttga gttcagctgc
1381    tctgagaagg aacaagaaat tgaaagactt aacaaactat gcgacagca tggacttctt
1441    ggtgaagtga actagacccg gaccagctcc cctcaaaaag aagacactgt ctcatgggcc
1501    tgtgctgtca cgagaggaac agctgcccct cctgggccgc ttggtgagag gtttggtttg
1561    ataccttgc ctccctcctg ccagcatgga ttctgggtgg acacagcctt gtggaaggtc
1621    cagtaccacc aagagctgcc catccactcc caccccacac tgtatcaaat gtatcacatt
1681    ttctcatgtt gaacacttta gccttaattg aaaatgagca acaaagctgg acaattgcta
1741    gttgtatata aatttaatc tcaccgaatg tacagttttc aaatttcacg tgtatattaa
1801    ggaactgatg catctgagca ttctgaaaga aagaaaaaga agctacttta gctgccaccc
1861    cattctagaa aagtctctta ttttcaagct gttctaaata gcttcgtctc agtttcccca
1921    aaaggggtac ccaggccccct cctctgtgtg ccccagctgc atcagccagc ttctaggtgg
1981    ctccattgtt ttctgccacc tgacaacatt tttcctcaat tactgtacaa ctactgtata
2041    aaataaaaca actactgtat aaaataaact ctctcttttc cctggaaaaa aaaaaaaaaa
2101    aaa
```

Human BIC isoform 2
cds 745-1455

FIG._9

```
  1    matwdekavt rrakvapaer mskflrhftv vgddyhawni nykkweneee eeeeeqpppt
 61    pvsgeviiic lvvldallvl aelildlkii qpdknnyaam vfhymsitil vffmmeiifk
121    lfvfrleffh hkfeildavv vvvsfildiv llfqehqfea lgllillrlw rvariingii
181    isvktrserq llrlkqmnvq laakiqhlef scsekeqeie rlnkllrqhg llgevn
```

Human BIC isoform 2
236 amino acids

FIG._10

MODULATORS OF LEUKOCYTE ACTIVATION, BIC COMPOSITIONS AND METHODS OF USE

FIELD OF THE INVENTION

The present invention relates to leukocyte activation, and provides nucleic acids and proteins which are capable of modulating leukocyte activation. The invention concerns disorders related to the dysfunction and dysregulation of leukocyte activation. These disorders include autoimmune diseases, acute and chronic inflammatory diseases, lymphomas, and leukemias. The invention further concerns the immune response of a host receiving a transplant. The invention further concerns disorders related to the dysfunction or dysregulation of BIC.

BACKGROUND OF THE INVENTION

The immune response comprises a cellular response and a humoral response. The cellular response is mediated largely by T lymphocytes (alternatively and equivalently referred to herein as T-cells), while the humoral response is mediated by B lymphocytes (alternatively and equivalently referred to herein as B-cells).

B-cells produce and secrete antibodies in response to the presentation of antigen and MHC class II molecules on the surface of antigen presenting cells. Antigen presentation initiates B-cell activation with the engagement of the B-cell receptor (BCR) at the cell's surface. Following engagement, the BCR relays signals that are propagated through the cell's interior via signal transduction pathways. These signals lead to changes in B-cell gene expression and physiology, which underlie B-cell activation.

T-cells produce costimulatory molecules, including cytokines, that augment antibody production by B-cells during the humoral immune response. Cytokines also play a role in modulating the activity of T-cells themselves. Many T-cells act directly to engulf and destroy cells or agents that they recognize by virtue of the cell surface proteins they possess. The engagement of cell surface receptors on T-cells results in the propagation of intracellular signals that provoke changes in T-cell gene expression and physiology, which underlie the cellular immune response.

Antigen recognition alone is usually not sufficient to initiate a complete effector T or B-cell response. The generation of many B-cell responses to antigen is dependent upon the interaction of B-cells with CD4+ helper T-cells directed against the same antigen. These helper T-cells express CD40L (CD154) which binds to the cell surface receptor, CD40, on resting B-cells. This interaction provides a critical activation signal to B-cells. Mutations in the CD40L lead to the X-linked immunodeficiency disorder hyper-IgM syndrome, which is characterized by low levels of IgA and IgG, normal to elevated levels of IgM, absence of germinal center formation, and decreased immune response. In addition, transgenic mice lacking CD40 exhibit reduced graft rejection. (Zanelli et al., Nature Medicine, 6: 629–630, 2000; Schonbeck et al., Cell Mol Life Sci, 58:4–43, 2001).

Non-lymphocyte leukocytes and platelets are also activated by surface receptor engagement in immune response and in response to injury. For example, mast cells and basophils are activated by binding of antigen to surface IgE, while platelets are activated by the binding of thrombin to its receptor.

Intercellular communication between different types of lymphocytes, as well as between lymphocytes and non-lymphocytes in the normally functioning immune system is well known. Much of this communication is mediated by cytokines and their cognate receptors. Cytokine-induced signals begin at the cell surface with a cytokine receptor and are transmitted intracellularly via signal transduction pathways. Many types of cells produce cytokines, and cytokines can induce a variety of responses in a variety of cell types, including leukocytes. The response to a cytokine can be context-dependent as well as cell type specific.

Dysregulation of intercellular communication can perturb leukocyte activity and the regulation of immune responses. Such dysregulation is believed to underlie certain autoimmune disease states, hyper-immune states, and immune-compromised states. Such dysfunction may be cell autonomous or non-cell autonomous with respect to lymphocytes.

The activation of specific signaling pathways in leukocytes determines the quality, magnitude, and duration of immune responses. In response to transplantation, in acute and chronic inflammatory diseases, and in autoimmune responses, it is these pathways that are responsible for the induction, maintenance and exacerbation of undesirable leukocyte responses. Identification of these signaling pathways is desirable in order to provide diagnostic and prognostic tools, as well as therapeutic targets for modulating leukocyte function in a variety of disorders or abnormal physiological states. In addition, the ability to modulate these pathways and suppress normal immune responses is often desirable, for example in hosts receiving a transplant.

A number of signals are known to regulate cellular functions by modulating the flow of cations through cell membranes. The flow of ions through the lipid bilayers of membranes is effected by ion channels. Ion channels are fundamental to cellular functions such as transmission of signals in the nervous system, cell division, and the production of antibodies by lymphocytes.

The forces that influence the movement of ions through a channel are electrical and chemical. The electrical force is the electrical potential across the membrane, the chemical force is the difference in concentration of an ion on the two sides of the membrane: the combination of the two is the electrochemical gradient for an ion. If the electrochemical gradient for an ion is not zero, ions will flow through a channel when it opens if the channel is permeant to that ion.

There are many varieties of ion channels that differ in their selectivity, methods of gating, conductance and kinetic properties. Some channels are selectively permeant to particular cations, including sodium, potassium, and calcium. Other are selective for particular anions, such as chloride. Channels are classified according to the ions that pass through them most freely. For example, sodium channels are more permeable to sodium than to any other cations or anions.

Channels are also classified according to the way in which their open/closed conformations are regulated, i.e., how they are gated. For example, voltage-activated channels open or close in response to changes in membrane potential. Some receptors are ligand-gated channels and are opened when ligands such as neurotransmitters bind to their surface. Other channels are indirectly linked to receptors by second messenger systems, which regulate channel opening and closing.

Channels can also have very different conductances. Conductance, the reciprocal of resistance, is a measure of the ease with which ions pass through a channel and is given by the ratio of the current to the driving force. The conductance of different channels can range from picosiemens to hundreds of picosiemens (corresponding to resistances of $10^9$ to $10^{12}$ ohms). Finally, channels can have very different "duty cycles". Some are open most of the time while others open infrequently. Some flicker rapidly between open and closed states while others do not. Changes in the environment of channels (e.g., the presence of drugs) can change these characteristics. Indeed it is becoming clear that many drugs exert their effects on cells and organs by binding to surface receptors and influencing channel behaviour.

Ion channels are useful pharmacological targets. A number of currently used pharmaceuticals act on ion channels. Calcium channel blockers are used as anti-angina and antihypertensive agents. Barbiturates cause sleep and inhibit epileptic seizures by increasing the movement of chloride ions through gamma-amininobutyric acid (GABA)-activated channels. Similarly, benzodiazepines relieve anxiety and produce anaesthesia by increasing GABA receptor activity and chloride ion conductance. Lymphocytes express a variety of cation channels, including potassium and calcium ion channels. A prolonged rise in intracellular calcium is required for lymphocyte activation, and the blockade of voltage-gated potassium channels and calcium-sensitive potassium channels inhibits antigen-induced activation of lymphocytes, likely by inducing membrane depolarization and thereby diminishing calcium influx (Lewis et al., Ann. Rev. Immunol., 13:623–653, 1995).

One manner by which intracellular calcium regulates lymphocyte activation is through the regulation of calcineurin activity. Calcineurin is a calcium-sensitive protein serine/threonine phosphatase comprised of a catalytic and a regulatory subunit. Calcineurin is activated by the binding of Ca2+/calmodulin, and is inhibited by the immunosuppressants FK506 and cyclosporin A. Binding of cyclosporin to calcineurin blocks substrate access to the active site of the phosphatase (Liu et al., Cell, 66: 807, 1991).

The activation of calcineurin is an important regulatory step in lymphocyte activation. Calcineurin regulates phosphorylation of the nuclear factor in activated T-cells (NFAT) transcription factor, and thereby regulates nuclear import of NFAT and its ability to regulate transcription. The expression of many factors involved in lymphocyte activation, including cytokines (such as IL-2) and cell surface molecules (eg. CD40L) lies downstream of NFAT activation. (see Klee et al., J Biol Chem., 273:13367, 1998; Stankunas et al., Cold Spring Harbor Symposia Quant. Biol., 64: 505–516, 1999).

The identification of cation channels associated with lymphocyte activation is desirable for the development of therapeutics that modulate the activity of such channels, which may be used for the treatment of autoimmune disorders, acute and chronic inflammatory disorders, and the management of immune responses in a host receiving a graft.

SUMMARY OF THE INVENTION

The present invention provides compositions and methods for modulating leukocyte activation. Compositions and methods for the treatment of disorders related to leukocyte dysfunction and dysregulation are also provided. Prophylactics and methods for the prevention of such disorders are also provided. Also provided are compositions and methods for the diagnostic and prognostic determination of such disorders. Further provided are assays for the identification of bioactive agents capable of modulating leukocyte activation.

Accordingly, in one aspect, the invention provides BIC nucleic acids which are capable of modulating leukocyte activation. In another aspect, the invention provides BIC proteins capable of modulating leukocyte activation.

In a preferred embodiment, a BIC protein provided herein is a transmembrane cation channel comprising four transmembrane domains. In a preferred embodiment, a BIC protein provided herein comprises an N-terminus which is intracellular. In a preferred embodiment, a BIC protein provided herein comprises a C-terminus which is intracellular. In an especially preferred embodiment, a BIC protein provided herein comprises an N-terminus and a C-terminus which are both intracellular. In a preferred embodiment, such a BIC protein comprises an amino acid sequence having at least about 85%, more preferably at least about 90%, more preferably at least about 95%, more preferably at least about 98% identity to the amino acid sequence set forth by residues 21–273 or 1–273 in SEQ ID NO:2. In an especially preferred embodiment, the BIC protein comprises the amino acid sequence set forth by residues 21–273 or 1–273 in SEQ ID NO:2.

In a preferred embodiment, a BIC protein provided herein has homology to the ion transport protein family described at NCBI conserved domain database no. Pfam00520.4. Among these proteins are sodium, potassium, and calcium channels having six transmembrane helices in which the last two helices flank a loop which determines ion selectivity. In some subfamilies (e.g. sodium channels) the domain is repeated four times, whereas in others (e.g. potassium channels) the protein forms as a tetramer in the membrane.

In a preferred embodiment, is present in the plasma membrane of a mammalian cell, preferably a human cell, preferably a lymphocyte.

In a preferred embodiment, a BIC protein provided herein is capable of modulating potassium conductance in a lymphocyte. In another preferred embodiment, a BIC protein provided herein is capable of modulating calcium conductance in a lymphocyte. In another preferred embodiment, a BIC protein provided herein is capable of modulating sodium conductance in a lymphocyte.

In a preferred embodiment, a BIC protein provided herein is capable of modulating T-cell receptor (TCR)-induced expression of CD69.

In a preferred embodiment, a BIC protein provided herein is capable of modulating B-cell receptor (BCR)-induced expression of CD69.

In a preferred embodiment, a BIC protein provided herein is capable of modulating BCR-induced activation of the immunoglobulin heavy chain gene (IgH) promoter.

In a preferred embodiment, a BIC protein provided herein is capable of modulating BCR-induced immunoglobulin production.

In a preferred embodiment, a BIC protein provided herein is capable of modulating a sustained increase in intracellular calcium levels induced by antigen receptor activation in lymphocytes.

In a preferred embodiment, a BIC protein provided herein is capable of modulating antigen receptor-induced calcineurin activity in lymphocytes.

In a preferred embodiment, a BIC protein provided herein is capable of modulating IL-4 induced CD23 expression. In another preferred embodiment, a BIC protein provided herein is capable of modulating CD40L-induced CD23 expression. In another preferred embodiment, a BIC protein provided herein is capable of modulating CD23 expression induced by the combination of CD40L and IL-4.

In a preferred embodiment, a BIC protein provided herein is capable of modulating surface Ig expression, preferably surface IgM expression, in a resting lymphocyte.

In a preferred embodiment, a BIC nucleic acid provided herein is expressed in the following tissues and cells in decreasing order of abundance of expression: testis, spleen, bone marrow, A5T4 cells, heart, placenta, skeletal muscle, uterus, PBMCs, lung, adrenal gland, small intestine, thymus, liver, trachea, colon, cerebellum, prostate, whole brain, salivary gland, thyroid, HL-60, kidney, Jurkat, pancreas, PhoenixA cells, MCF-7 cells, Huh7 cells.

The present invention also provides isolated polypeptides which specifically bind to a BIC protein. In one embodiment, the polypeptide is an antibody. In a preferred embodiment, the polypeptide is a monoclonal antibody. In a preferred embodiment, the monoclonal antibody is capable of reducing or eliminating the activity of BIC. In another preferred embodiment, the antibody is capable of increasing or altering the activity of BIC.

Also provided herein are methods of screening for a bioactive agent capable of binding to a BIC protein. The methods comprise combining a BIC protein and a candidate bioactive agent and determining the binding of candidate agent to BIC protein. In one embodiment, the method involves identifying the candidate agent. In a preferred embodiment, the BIC protein is inserted into a membrane, forming a transmembrane protein comprising four transmembrane domains.

Also provided herein are methods of screening for a bioactive agent capable of interfering with the binding of a BIC protein. The methods comprise combining a candidate bioactive agent, a BIC protein, and a BIC binding partner which will bind to BIC in the absence of candidate agent, and determining the binding of BIC to binding partner in the presence of candidate bioactive agent. In a preferred embodiment, the BIC binding partner is an anti-BIC antibody, further described herein. In another embodiment, the BIC binding partner is a known cation channel modulator or blocker. In another embodiment, the BIC binding partner is another BIC protein, or other cation channel subunit. In a preferred embodiment, the method involves determining the binding of BIC to binding partner in the presence and absence of candidate bioactive agent. In one embodiment, BIC and BIC binding partner are combined first. In one embodiment, the method involves identifying the candidate agent. In a preferred embodiment, the BIC protein is inserted into a membrane, forming a transmembrane protein comprising four transmembrane domains, and candidate agents are screened for their ability to interfere with binding of the BIC protein to BIC binding partner.

Also provided herein are methods of screening for a bioactive agent capable of increasing the binding of a BIC protein. The methods comprise combining a candidate bioactive agent, a BIC protein, and a BIC binding partner which will bind to BIC in the absence of candidate agent, and determining the binding of BIC to binding partner in the presence of candidate bioactive agent. In a preferred embodiment, the BIC binding partner is an anti-BIC antibody, further described herein. In another embodiment, the BIC binding partner is a known cation channel modulator or blocker. In another embodiment, the BIC binding partner is another BIC protein, or other cation channel subunit. In a preferred embodiment, the method involves determining the binding of BIC to binding partner in the presence and absence of candidate bioactive agent. In one embodiment, BIC and BIC binding partner are combined first. In one embodiment, the method involves identifying the candidate agent. In a preferred embodiment, the BIC protein is inserted into a membrane, forming a transmembrane protein comprising four transmembrane domains, and candidate agents are screened for their ability to increase the binding of BIC protein to BIC binding partner.

Also provided herein are methods of screening for a bioactive agent capable of modulating the activity of a BIC protein. In a preferred embodiment, the method comprises contacting a candidate bioactive agent to a cell comprising a recombinant BIC nucleic acid and expressing a BIC protein. In a preferred embodiment, the method comprises contacting a library of candidate bioactive agents to a plurality of cells comprising a recombinant BIC nucleic acid and expressing a BIC protein. In a preferred embodiment, the method comprises determining cation conductance of the plasma membrane of such a cell in the presence of candidate agent. In a preferred embodiment, the method comprises determining changes in intracellular or extracellular cation concentration in such a cell in the presence of candidate agent using a cation sensitive dye. In a preferred embodiment, the method comprises measuring changes in membrane potential in such a cell in the presence of candidate agent, for example using a voltage sensitive dye. In a preferred embodiment, the method involves patch-clamping such a cell and measuring current in the presence of candidate agent. In a preferred embodiment, the method involves patch-clamping a portion of the membrane comprising an expressed BIC protein and measuring current in the presence of candidate agent. In a preferred embodiment, the method involves pulling such a patch from the cell and measuring current in the presence of candidate agent. In a preferred embodiment, intracellular recording is done in such a cell in the presence of candidate agent and changes in membrane potential are measured. In some preferred embodiments, channel blockers or modulators are employed. In some preferred embodiments, impermeant cations are substituted for permeant cations.

Also provided herein are methods of screening for a bioactive agent capable of modulating lymphocyte activation.

In a preferred embodiment, the methods comprise determining the ability of a candidate agent to bind to BIC.

In a preferred embodiment, the methods comprise detecting binding of candidate agent to BIC protein, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Bioactive agents that inhibit lymphocyte activation in these assays are useful as immunosuppressants.

In another preferred embodiment, the methods comprise determining the ability of a candidate agent to modulate the binding of BIC to a BIC binding partner.

In a preferred embodiment, the methods comprise detecting modulation of BIC protein binding to a BIC binding partner in the presence of candidate agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Bioactive agents that inhibit lymphocyte activation in these assays are useful as immunosuppressants.

In another preferred embodiment, the methods comprise determining the ability of a candidate bioactive agent to modulate the activity of a BIC protein.

In a preferred embodiment, the methods comprise determining a change in cation conductance of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, the methods comprise detecting a change in membrane potential of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, the methods comprise detecting a change in transmembrane current of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, the methods comprise detecting a change in intracellular or extracellular cation concentration, i.e., to one side or the other of a membrane comprising BIC, in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, the methods involve expressing a recombinant BIC nucleic acid in a cell.

In a preferred embodiment, the methods involve inducing overexpression of endogenous BIC in a cell.

Bioactive agents that inhibit lymphocyte activation in these assays are useful as immunosuppressants.

In a preferred embodiment, the methods comprise detecting binding of candidate agent to BIC protein, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

Bioactive agents that inhibit CD23 induction in these assays are useful as immunosuppressants.

In a preferred embodiment, the methods comprise detecting modulation of the binding of BIC protein to a BIC binding partner in the presence of candidate agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

Bioactive agents that inhibit CD23 induction in these assays are useful as immunosuppressants.

In a preferred embodiment, the methods comprise determining a change in cation conductance of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, the methods comprise detecting a change in membrane potential of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, the methods comprise detecting a change in transmembrane current of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL4, CD40L, and the combination of IL-4 and CD40L.

In a preferred embodiment, the methods comprise detecting a change in intracellular or extracellular cation concentration, i.e., to one side or the other of a membrane comprising BIC, in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, the methods involve expressing a recombinant BIC nucleic acid in a cell.

In a preferred embodiment, the methods involve inducing overexpression of endogenous BIC in a cell.

Bioactive agents that inhibit CD23 induction in these assays are useful as immunosuppressants.

In a preferred embodiment, the methods comprise detecting binding of candidate agent to BIC protein, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise detecting modulation of the binding of BIC protein to a BIC binding partner in the presence of candidate agent, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise determining a change in cation conductance of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in membrane potential of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in transmembrane current of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in intracellular or extracellular cation concentration, i.e., to one side or the other of a membrane comprising BIC, in the presence of candidate bioactive agent, contacting the candidate bioactive agent to a resting B-lymphocyte, and determining the level of surface Ig expression, preferably surface IgM expression, in the cell.

Particularly preferred are Ramos cells and primary B-cells.

In a preferred embodiment, the methods involve expressing a recombinant BIC nucleic acid in a cell.

In a preferred embodiment, the methods involve inducing overexpression of endogenous BIC in a cell.

Agents that decrease surface Ig expression in resting B-cells are particularly preferred, and are useful as immunosuppressants.

In a preferred embodiment, candidate bioactive agents used in these assays are small molecule chemical compounds, from about 100 to about 1500, more preferably about 100 to about 1200, more preferably about 100 to about 1000 more preferably about 200 to about 500 daltons.

In a preferred embodiment, a library of candidate bioactive agents is contacted to BIC protein.

In a preferred embodiment, a library of candidate bioactive agents is contacted to a plurality of cells comprising BIC protein.

In a preferred embodiment, determining lymphocyte activation in the methods herein comprises determining the level of expression of a surface marker which is associated with activation of the lymphocyte, in the presence of candidate agent. In a preferred embodiment, the surface marker is selected from the group consisting of CD40L, CD23, CD69, CD80 and CD86. In an especially preferred embodiment, the surface marker is CD69 or CD23.

In another preferred embodiment, determining lymphocyte activation in the methods herein comprises determining the level of activity of a promoter in the presence of candidate agent, which activity correlates with lymphocyte activation in the absence of candidate agent. In a preferred embodiment the promoter is an NFAT-responsive promoter, such as the IL-2 promoter. In another preferred embodiment, the promoter is the immunoglobulin heavy chain gene promoter.

In a preferred embodiment, determining lymphocyte activation, including CD23 induction, is done using a FACS machine. In a preferred embodiment, lymphocytes are sorted by FACS. A FACS machine may be used to determine the level of expression of a surface marker or intracellular marker which normally correlates with lymphocyte activation, or the level of activity of a promoter which normally correlates with lymphocyte activation, or the intracellular calcium level, or other indicators of lymphocyte activation, including those discussed herein. Sorting of lymphocytes may be done on these bases.

Also provided herein are methods for modulating lymphocyte activation in a patient having a lymphocyte activation disorder, comprising administering to a patient having a lymphocyte activation disorder a medicament comprising a modulator of BIC activity.

Also provided herein are methods for inhibiting B-cell and T-cell activation in a patient having an autoimmune disease, comprising administering to a patient having an autoimmune disease a medicament comprising a modulator of BIC activity.

Also provided herein are methods for inhibiting B cell and T cell activation in a patient having an autoimmune disease, comprising administering to a patient having an autoimmune disease a medicament comprising an immunosuppressant obtained by the screening methods provided herein.

Also provided herein are methods for inhibiting immunoglobulin production in a patient having an autoimmune disease, comprising administering to a patient having an autoimmune disease a medicament comprising a modulator of BIC activity.

Also provided herein are methods for inhibiting immunoglobulin production in a patient having an autoimmune disease, comprising administering to a patient having an autoimmune disease a medicament comprising an immunosuppressant identified by the methods provided herein.

Also provided herein are methods for prolonging the survival of a graft in a mammalian host, comprising administering to a mammalian host receiving a graft a medicament comprising a modulator of BIC activity.

Also provided herein are methods for prolonging the survival of a graft in a mammalian host, comprising administering to a mammalian host receiving a graft a medicament comprising an immunosuppressant identified by the methods provided herein.

In a preferred embodiment, provided herein are small molecule chemical compositions useful for the prevention and treatment of acute inflammatory disorders, chronic inflammatory disorders, autoimmune disorders, and transplant rejection.

BRIEF DESCRIPTION OF THE DRAWINGS

FIG. 1 shows nucleotide sequence of human BIC, SEQ ID NO:1.

FIG. 2 shows amino acid sequence of human BIC, SEQ ID NO:2. The structure of BIC is shown.

FIG. 3 shows results of experiments in which BIC HIT (SEQ ID NO:1, nucleotides 189–968) was expressed in the BJAB (B-cell) cell line and the Jurkat (T-cell) cell line, and BCR- or TCR-induced CD69 expression was measured by FACS machine using a labelled anti-CD69 antibody. The results demonstrate that BIC HIT inhibits BCR- and TCR-induced lymphocyte activation, as measured by CD69 expression.

FIG. 4 is a table of human autoimmune diseases.

FIG. 5 shows an expression profile of BIC mRNA in blood cell subsets in the resting and activated states.

FIG. 6 shows the results of experiments in which BIC was expressed in the BJAB cell line and the Jurkat cell line, and BCR-, or TCR- and ionomycin-induced calcium flux was measured by FACS machine using a calcium-sensitive dye. The results demonstrate that BIC HIT (SEQ ID NO:1, nucleotides 189–968) and full length BIC (protein at SEQ ID NO:2) both inhibit BCR-induced calcium flux, but do not inhibit TCR-induced calcium flux in Jurkat cells.

FIG. 7 shows the results of experiments in which BIC was expressed in the Ramos cell line, and CD23 expression induced by the combination of CD-40L and IL-4 was measured by FACS machine using a labelled anti-CD23 antibody. The results demonstrate that BIC HIT (SEQ ID NO:1, nucleotides 189–968) and full length BIC (protein at SEQ ID NO:2) both inhibit CD23 induction.

FIG. 8 shows the results of experiments in which BIC was expressed in the Ramos cell line, and surface IgM expression in resting cells was determined by FACS machine using a labelled anti-IgM antibody. The results demonstrate that BIC HIT (SEQ ID NO:1, nucleotides 189–968) and full length BIC (protein at SEQ ID NO:2) decrease surface IgM expression in resting Ramos cells.

FIG. 9 shows the nucleotide sequence of human BIC isoform 2 (SEQ ID NO:3).

FIG. 10 shows the amino acid sequence of human BIC isoform 2 (SEQ ID NO:4). Comparison of the amino acid sequence of isoform 2 and BIC (SEQ ID NOs:4 and 2) reveals isoform 2 has a 37 amino acid gap, from residue 66–102, inclusive, in SEQ ID NO:2.

DETAILED DESCRIPTION OF THE INVENTION

The present invention provides compositions and methods for modulating leukocyte activation. Compositions and methods for the treatment of disorders related to the dysfunction and dysregulation of leukocyte activation are also provided. Prophylactics and methods for the prevention of such disorders are also provided. Also provided are compositions and methods for the diagnostic and prognostic determination of such disorders. Further provided are assays for the identification of bioactive agents capable of modulating leukocyte activation.

In accordance with these objectives, in one aspect, the present invention provides BIC nucleic acids which are capable of modulating leukocyte activation. Also in accordance with these objectives, in another aspect, the invention provides BIC proteins capable of modulating leukocyte activation.

A BIC protein of the present invention may be identified in several ways. "Protein" in this sense includes proteins, polypeptides, and peptides. A BIC protein may be identified by its ability to bind to BIC binding partners as described herein. A BIC protein may be identified by its ability to form a four transmembrane domain cation channel. A BIC protein may also be identified by its ability to alter membrane potential when expressed in a host cell. A BIC protein may also be identified by its ability to alter cation conductance when expressed in a host cell. A BIC protein may also be identified by its ability to alter transmembrane current when expressed in a host cell. A BIC protein may also be identified by amino acid sequence identity or similarity to SEQ ID NO:2 or 4, or by the sequence identity or similarity of its encoding nucleic acid to SEQ ID NO:1 or 3.

BIC nucleic acids and proteins may initially be identified by sequence identity or similarity to SEQ ID NOs:1–4, as further described below. In a preferred embodiment, BIC nucleic acids and BIC proteins have sequence identity or similarity to the sequences provided herein and one or more BIC bioactivities described herein. Such sequence identity or similarity can be based upon the overall nucleic acid or amino acid sequence.

In a preferred embodiment, a BIC protein provided herein comprises an amino acid sequence having at least about 85%, more preferably at least about 90%, more preferably at least about 95%, more preferably at least about 98% identity to the amino acid sequence set forth in SEQ ID NO:2 or 4. In a preferred embodiment, the BIC protein comprises the amino acid sequence set forth in SEQ ID NO:2 or 4. Preferably, the BIC protein also possesses one or more BIC bioactivities described herein.

BIC protein consisting of SEQ ID NO:4 has been previously identified as an ion transport protein consisting of four transmembrane regions (WO 01/46258).

BIC protein consisting of SEQ ID NO:2 has been previously identified (Genbank Accession No. BC009731).

Fragments are included in the definition of BIC proteins. In a preferred embodiment, a BIC protein provided herein comprises an amino acid sequence having at least about 85%, more preferably at least about 90%, more preferably at least about 95%, more preferably at least about 98% identity to a portion of the amino acid sequence set forth in SEQ ID NO:2. In an especially preferred embodiment, the BIC protein comprises a portion of the amino acid sequence set forth in SEQ ID NO:2. Portion, or fragment, in this sense includes sequences from at least 2 amino acids up to the full length sequence in SEQ ID NO:2 minus one amino acid at either the N- or C-terminus.

In a preferred embodiment, a BIC protein provided herein comprises four transmembrane domains. In a preferred embodiment, such a BIC protein comprises an amino acid sequence having at least about 85%, more preferably at least about 90%, more preferably at least about 95%, more preferably at least about 98% identity to the amino acid sequence set forth by residues 21–273 in SEQ ID NO:2. In an especially preferred embodiment, the BIC protein comprises the amino acid sequence set forth by residues 21–273 in SEQ ID NO:2.

In a preferred embodiment, the invention provides BIC protein fragments which correspond to non-transmembrane portions of the BIC protein which are flanked by transmembrane segments (intracellular or extracellular loops, where the membrane is the plasma membrane), or are flanked by a transmembrane segment at one end and the N-terminus or C-terminus at the other end (i.e. fragment comprises the N-terminus ir C-terminus).

In one aspect, the present invention provides BIC nucleic acids, including BIC nucleic acids encoding BIC proteins.

In the case of a BIC nucleic acid encoding a BIC protein, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. A BIC nucleic acid of the present invention comprises a nucleic acid sequence that preferably has greater than about 75% identity to the nucleic acid sequence set forth in SEQ ID NO:1, more preferably greater than about 80%, more preferably greater than about 85% and most preferably greater than 90%. In some embodiments the sequence identity will be as high as about 93 to 95 or 98%.

In a preferred embodiment, a BIC nucleic acid encodes a BIC protein. As will be appreciated by those in the art, due to the degeneracy of the genetic code, an extremely large number of nucleic acids may be made, all of which encode the BIC proteins of the present invention. Thus, having identified a particular amino acid sequence, those skilled in the art could make any number of different nucleic acids, by simply modifying the sequence of one or more codons in a way which does not change the amino acid sequence of the BIC protein.

In a preferred embodiment, the BIC nucleic acid comprises a nucleic acid sequence having at least about 85%, more preferably at least about 90%, more preferably at least about 95%, more preferably at least about 98% identity to the nucleic acid sequence set forth in SEQ ID NO:1. In a preferred embodiment, the BIG nucleic acid comprises the nucleic acid sequence set forth in SEQ ID NO:1. In a preferred embodiment, the BIC nucleic acid encodes a BIC protein.

In a preferred embodiment, the BIC nucleic acid comprises a nucleic acid sequence having at least about 85%, more preferably at least about 90%, more preferably at least about 95%, more preferably at least about 98% identity to the nucleic acid sequence set forth by residues 133–954 in SEQ ID NO:1. In an especially preferred embodiment, the BIC nucleic acid comprises residues 133–954 in SEQ ID NO:1.

In a preferred embodiment, the BIC nucleic acid comprises a nucleic acid sequence having at least about 85%, more preferably at least about 90%, more preferably at least about 95%, more preferably at least about 98% identity to the nucleic acid sequence set forth by residues 189–968 in SEQ ID NO:1. In an especially preferred embodiment, the BIC nucleic acid comprises residues 189–968 in SEQ ID NO:1.

In a preferred embodiment, the BIC nucleic acid comprises a nucleic acid sequence having at least about 85%, more preferably at least about 90%, more preferably at least about 95%, more preferably at least about 98% identity to the nucleic acid sequence set forth by residues 745–1455 in SEQ ID NO:3. In an especially preferred embodiment, the BIC nucleic acid comprises residues 745–1455 in SEQ ID NO:3.

In a preferred embodiment, the invention provides BIC proteins encoded by BIC nucleic acids provided herein.

In a preferred embodiment, the present invention provides BIC nucleic acids encoding BIC proteins. In a preferred embodiment, a BIC nucleic acid comprises a nucleic acid sequence encoding an amino acid sequence having at least about 85%, more preferably at least about 90%, more preferably at least about 95%, more preferably at least about 98% identity to the amino acid sequence set forth by residues 21–273 or 1–273 in SEQ ID NO:2.

In an especially preferred embodiment, a BIC nucleic acid provided herein encodes a BIC protein comprising the amino acid sequence set forth by residues 21–273 or 1–273 in SEQ ID NO:2.

In a preferred embodiment, a BIC nucleic acid comprises a nucleic acid sequence encoding an amino acid sequence having at least about 85%, more preferably at least about 90%, more preferably at least about 95%, more preferably at least about 98% identity to the amino acid sequence set forth in SEQ ID NO:4.

In an especially preferred embodiment, a BIC nucleic acid provided herein encodes a BIC protein comprising the amino acid sequence set forth in SEQ ID NO:4.

In one embodiment, the BIC nucleic acid is determined through hybridization studies. Thus, for example, nucleic acids which hybridize under high stringency conditions to the nucleic acid sequences shown in SEQ ID NO:1 or 3, or their complements, or fragments thereof or their complements, are considered BIC nucleic acids. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Molecular Cloning, A Laboratory Manual, Sambrook et al., *Molecular Cloning, A Laboratory Manual*, 3rd edition, 2001, Cold Spring Harbor Press, Cold Spring Harbor, N.Y.; and Tijssen, supra.

Also provided herein are BIC antisense nucleic acids which will hybridize under high stringency conditions to a BIC nucleic acid comprising the nucleic acid sequence set forth in SEQ ID NO:1 or 3. In a preferred embodiment, the BIC antisense nucleic acid inhibits expression of BIC protein. In a preferred embodiment, the BIC antisense nucleic acid inhibits BIC protein activity.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology*, 266: 460–480 (1996)]. WU-BLAST-2 uses several search parameters, most of which are set to the default values. The adjustable parameters are set with the following values: overlap span= 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the BIC protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

In a preferred embodiment, a BIC protein provided herein has one or more of the following characteristics: permeable to cations, preferably selected from potassium, calcium and sodium; the ability to depolarize cell membrane; the ability to alter membrane potential; the ability to modulate transmembrane current; the ability to modulate intracellular cation concentration, preferably selected from potassium, sodium and calcium; the ability to alter cellular conductance of cations, preferably selected from potassium, calcium and sodium; the ability to modulate leukocyte and platelet activation; the ability to modulate antigen-receptor induced CD69 expression in lymphocytes; the ability to modulate immunoglobulin heavy chain gene (IgH) promoter activity in B lymphocytes; and the ability to modulate NFAT activity in lymphocytes. Homology and identity to SEQ ID NO:2 and 4 can be determined as described above. In one embodiment, homology and identity are determined by performing a Blastp search in Genbank's non-redundant protein database using default parameters. In another embodiment, homology and identity are determined using the following database and parameters: Database: Non-redundant GenBank CDS translations+PDB+SwissProt+Spupdate+PIR; Lambda of 0.316, K of 0.133 and H of 0; Gapped Lambda of 0.27, K of 0.047, and H of 4.94e-324; Matrix is BLOSUM62; Gap Penalties: Existence: 11, Extension: 1.

In a preferred embodiment, the BIC protein comprises the amino acid sequence set forth in SEQ ID NO:2. The characteristics described below also apply to other preferred BIC proteins provided herein.

In some preferred embodiments, the BIC protein binds to a BIC binding partner, preferably an anti-BIC antibody, a cation channel modulator or blocker, or another BIC protein, or other cation channel subunit.

BIC proteins of the present invention may be shorter or longer than the amino acid sequence encoded by the nucleic acid sequences shown in SEQ ID NOs:1 and 3. Thus, in a preferred embodiment, included within the definition of BIC proteins are portions or fragments of the amino acid sequences encoded by the nucleic acid sequences provided herein. In one embodiment herein, fragments of BIC proteins are considered BIC proteins if a) they share at least one antigenic epitope; b) have at least the indicated sequence identity; c) and preferably have BIC protein activity as further defined herein. In some cases, where the sequence is used diagnostically, that is, when the presence or absence of BIC nucleic acid is determined, only the indicated sequence identity is required. The nucleic acids of the present invention may also be shorter or longer than the sequences in SEQ ID NOs:1 and 3. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, BIC proteins can be made that are longer than those depicted in SEQ ID NOs:2 and 4; for example, by the addition of epitope or purification tags, the addition of other fusion sequences, or the elucidation of additional coding and non-coding sequences. As described below, the fusion of a BIC peptide to a fluorescent protein, such as Blue Fluorescent Protein (BFP) or Green Fluorescent Protein (GFP), including those of Aquorea and Renilla species, is particularly preferred. In another preferred embodiment, the fluorescent protein is a GFP from Ptilosarcus. In another preferred embodiment, the fluorescent protein is a GFP homologue from Anthozoa species (Matz et al., Nat. Biotech., 17:969–973, 1999).

In a preferred embodiment, when a BIC protein is to be used to generate antibodies, a BIC protein must share at least one epitope or determinant with the full length protein. By "epitope" or "determinant" herein is meant a portion of a protein which will generate and/or bind an antibody. Thus, in most instances, antibodies made to a smaller BIC protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. Preferred epitopes are derived from the regions of the BIC protein which are exposed (i.e., not imbedded in membrane) when the BIC protein forms a four transmembrane domain cation channel. Especially preferred are the regions exposed extracellularly when the BIC protein is inserted in a plasma membrane. In another embodiment, antibodies raised against regions exposed intracellularly when the BIC protein is inserted in a plasma membrane are provided.

In one embodiment, the antibodies to a BIC protein are capable of reducing or eliminating the biological function of the BIC proteins described herein, as is described below. That is, the addition of anti-BIC antibodies (either polyclonal or preferably monoclonal) to BIC proteins (or cells containing BIC proteins) may reduce or eliminate their ability to modulate leukocyte and platelet activation. Generally, at least a 25% decrease in activity is preferred, with at least about 50% being particularly preferred and about a 95–100% decrease being especially preferred.

In another embodiment, anti-BIC antibodies which increase the activity of BIC or potentiate the activity of BIC (function activating antibodies) are provided. Function activating antibodies may increase cation conductance by BIC, increase the frequency at which BIC is in the open state, or increase the length of time BIC remains in the open state. By open state is meant the conformation of BIC which provides for the conductance of cations across a membrane.

The anti-BIC antibodies of the invention bind to BIC proteins. In a preferred embodiment, the antibodies specifically bind to BIC proteins. By "specifically bind" herein is meant that the antibodies bind to the protein with a binding constant in the range of at least $10^{-4}$–$10^{-4}$ $M^{-1}$, with a preferred range being $10^{-7}$–$10^{-9}$ $M^{-1}$. Antibodies are further described below.

The BIC proteins and BIC nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the Figures also include the complement of the sequence.

By the term "recombinant nucleic acid" herein is meant nucleic acid, originally formed in vitro, in general, by the manipulation of nucleic acid by endonucleases, in a form not normally found in nature. Thus an isolated BIC nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention. This includes nucleic acids which incorporate into the genome of a host cell.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a BIC protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides BIC protein variants. These variants fall into one or more of three classes: substitutional, insertional or deletional variants. These variants ordinarily are prepared by site specific mutagenesis of nucleotides in the DNA encoding a BIC protein, using cassette or PCR mutagenesis or other techniques well known in the art, to produce DNA encoding the variant, and thereafter expressing the DNA in recombinant cell culture as outlined above. However, variant BIC protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the BIC protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed BIC protein variants screened for the optimal combination of desired activity. Techniques for making substitution mutations at predetermined sites in DNA having a known sequence are well known, for example, M13 primer mutagenesis and PCR mutagenesis. Screening of the mutants is done using assays of BIC protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the BIC protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the BIC proteins as needed. Alternatively, the variant may be designed such that the biological activity of the BIC protein is altered. For example, glycosylation sites may be altered or removed, or pore sites, channel blocking sites, or ligand-binding sites may be altered or removed. Portions of the channel responsible for gating may be altered. Portions of the channel responsible for cation selectivity may be altered.

Covalent modifications of BIC polypeptides are included within the scope of this invention. One type of covalent modification includes reacting targeted amino acid residues of a BIC polypeptide with an organic derivatizing agent that is capable of reacting with selected side chains or the N- or C-terminal residues of a BIC polypeptide. Derivatization with bifunctional agents is useful, for instance, for crosslinking BIC to a water-insoluble support matrix or surface for use in the method for purifying anti-BIC antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the BIC polypeptide included within the scope of this invention comprises altering the native glycosylation pattern of the polypeptide. "Altering the native glycosylation pattern" is intended for purposes herein to mean deleting one or more carbohydrate moieties found in native sequence BIC polypeptide, and/or adding one or more glycosylation sites that are not present in the native sequence BIC polypeptide.

Addition of glycosylation sites to BIC polypeptides may be accomplished by altering the amino acid sequence thereof. The alteration may be made, for example, by the addition of, or substitution by, one or more serine or threonine residues to the native sequence BIC polypeptide (for O-linked glycosylation sites). The BIC amino acid sequence may optionally be altered through changes at the DNA level, particularly by mutating the DNA encoding the BIC polypeptide at preselected bases such that codons are generated that will translate into the desired amino acids.

Another means of increasing the number of carbohydrate moieties on the BIC polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the BIC polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of BIC comprises linking the BIC polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

BIC polypeptides of the present invention may also be modified in a way to form chimeric molecules comprising a BIC polypeptide fused to another, heterologous polypeptide or amino acid sequence. In one embodiment, such a chimeric molecule comprises a fusion of a BIC polypeptide with a tag polypeptide which provides an epitope to which an anti-tag antibody can selectively bind. In a preferred embodiment, such a tag is the "flag tag" described below. The epitope tag is generally placed at the amino- or carboxyl-terminus of the BIC polypeptide. The presence of such epitope-tagged forms of a BIC polypeptide can be detected using an antibody against the tag polypeptide. Also, provision of the epitope tag enables the BIC polypeptide to be readily purified by affinity purification using an anti-tag antibody or another type of affinity matrix that binds to the epitope tag. In an alternative embodiment, the chimeric molecule may comprise a fusion of a BIC polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an embodiment herein, BIC protein family members and BIC proteins from other organisms are cloned and expressed as outlined below. Thus, probe or degenerate polymerase chain reaction (PCR) primer sequences may be used to find other related BIC proteins from humans or other organisms. As will be appreciated by those in the art, particularly useful probe and/or PCR primer sequences include the unique areas of the BIC nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant BIC nucleic acid can be further used as a probe to identify and isolate other BIC nucleic acids. It can also be used as a "precursor" nucleic acid to make modified or variant BIC nucleic acids and proteins.

Of course, as will be recognized by the artisan, PCR may also be used to obtain large quantities of a desired BIC nucleic acid from a source comprising such a BIC nucleic acid.

Using the nucleic acids of the present invention which encode a BIC protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the BIC protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the BIC protein; for example, transcriptional and translational regulatory nucleic acid sequences from Bacillus are preferably used to express the BIC protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

BIC proteins of the present invention are produced by culturing a host cell transformed with an expression vector containing BIC nucleic acid encoding a BIC protein, under the appropriate conditions to induce or cause expression of the BIC protein. The conditions appropriate for BIC protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines.

In a preferred embodiment, the BIC proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for BIC protein into mRNA. A promoter will have a transcription initiating region, which is usually placed proximal to the 5' end of the coding sequence, and usually a TATA box, typically located 25–30 base pairs upstream of the transcription initiation site. The TATA box is thought to direct RNA polymerase 11 to begin RNA synthesis at the correct site. However, TATA-free transcription initiation is also well known. A mammalian promoter will also contain an upstream promoter element (enhancer element), typically located within 100 to 200 base pairs upstream of the TATA box, if present. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation. Examples of transcription terminator and polyadenylation signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, BIC proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of BIC protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the BIC protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, BIC proteins are produced in insect cells. Expression vectors for the transformation of insect cells, and in particular, baculovirus-based expression vectors, are well known in the art.

In a preferred embodiment, BIC protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The BIC protein may also be made as a fusion protein, using techniques well known in the art. Thus, for example, for the creation of monoclonal antibodies, if the desired epitope is small, the BIC protein may be fused to a carrier protein to form an immunogen. Alternatively, the BIC protein may be made as a fusion protein to increase expression, or for other reasons. For example, when the BIC protein is a BIC peptide, the nucleic acid encoding the peptide may be linked to other nucleic acid for expression purposes. Similarly, BIC proteins of the invention can be linked to protein labels, such as green fluorescent protein (GFP), red fluorescent protein (RFP), blue fluorescent protein (BFP), yellow fluorescent protein (YFP), etc.

In one embodiment, the BIC nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the BIC protein is purified or isolated after expression. BIC proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the BIC protein may be purified using a standard anti-BIC antibody column. Ultrafiltration and diafiltration techniques, in conjunction with protein concentration, are also useful. For general guidance in suitable purification techniques, see Scopes, R., *Protein Purification*, Springer-Verlag, N.Y. (1982). The degree of purification necessary will vary depending on the use of the BIC protein. In some instances no purification will be necessary.

Once expressed and purified if necessary, the BIC proteins and nucleic acids are useful in a number of applications.

The nucleotide sequences (or their complement) encoding BIC proteins have various applications in the art of molecular biology, including uses as hybridization probes, in chromosome and gene mapping and in the generation of antisense RNA and DNA. BIC protein nucleic acid will also be useful for the preparation of BIC proteins by the recombinant techniques described herein.

The full-length native sequence BIC protein gene, or portions thereof, may be used as hybridization probes for a cDNA library or genomic DNA library to isolate other genes (for instance, those encoding naturally-occurring variants of BIC protein or BIC protein from other species) which have a desired sequence identity to the BIC protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the BIC protein gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the BIC protein gene of the present invention can be used to screen libraries of human cDNA, genomic DNA or mRNA to determine which members of such libraries the probe hybridizes.

Nucleotide sequences encoding a BIC protein can also be used to construct hybridization probes for mapping the gene which encodes that BIC protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode BIC protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a BIC protein can be used to clone genomic DNA encoding a BIC protein in accordance with established techniques and the genomic sequences used to generate transgenic animals that contain cells which express the desired BIC DNA. In another embodiment, cDNA is used in the formation of a transgene. Methods for generating transgenic animals, particularly animals such as mice or rats, have become conventional in the art and are described, for example, in U.S. Pat. Nos. 4,736,866 and 4,870,009. Typically, particular cells would be targeted for the BIC protein transgene expression with tissue-specific enhancers. Transgenic animals that include a copy of a transgene encoding a BIC protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the BIC protein can be used to construct a BIC protein "knock out" animal which has a defective or altered gene encoding a BIC protein as a result of homologous recombination between the endogenous gene encoding a BIC protein and altered genomic DNA encoding a BIC protein introduced into an embryonic cell of the animal. For example, cDNA encoding a BIC protein can be used to clone genomic DNA encoding a BIC protein in accordance with established techniques. A portion of the genomic DNA encoding a BIC protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69.915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the BIC protein.

It is understood that the models described herein can be varied. For example, "knock-in" models can be formed, or the models can be cell-based rather than animal models.

Nucleic acid encoding the BIC polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnoloy* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al, *J. Biol. Chem.* 262, 4429–4432 (1987); and Wagner et a., *Proc. Natl. Acad. Sci. USA* 87, 3410–3414 (1990). For review of gene marking and gene therapy protocols see Anderson et al., *Science* 256, 808–813 (1992).

In a preferred embodiment, the BIC proteins, nucleic acids, variants, modified proteins, cells and/or transgenics containing the said nucleic acids or proteins are used in screening assays. Identification of the BIC proteins provided herein permits the design of drug screening assays for compounds that bind BIC proteins, interfere with BIC protein binding, modulate BIC activity, and modulate lymphocyte activation.

The assays described herein preferably utilize the human BIC protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, truncated BIC proteins may be used.

In a preferred embodiment, the methods comprise combining a BIC protein and a candidate bioactive agent, and determining the binding of the candidate agent to the BIC protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind BIC protein, may be used.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^{7-108}$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred, and 12 and 18 amino acids being most preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al, Eur. J. Biochem., 81:579 (1977); Letsinger, etal., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al, J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl. 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

For an example of how nucleic acids may be used as candidate agents to screen for a change in phenotype, see Holland et al., J. Exp. Med., 194:1263–1276, 2001. See also Hitoshi et al., Immunity, 8:461–471, 1998. Both of which are expressly incorporated herein by reference.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties or small molecule chemical compositions, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

Generally, in a preferred embodiment of the methods herein, for example for binding assays, the BIC protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the BIC protein is bound to the support, and a candidate bioactive agent is added to the assay. Alternatively, the candidate agent is bound to the support and the BIC protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the BIC protein may be done in a number of ways. In a preferred embodiment, the candidate bioactive agent is labelled, and binding determined directly. For example, this may be done by attaching all or a portion of the BIC protein to a solid support, adding a labelled candidate agent (for example a fluorescently labeled agent), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. BIC protein), such as an antibody. Under certain circumstances, there may be competitive binding as between the bioactive agent and the binding moiety, with the binding moiety displacing the bioactive agent. This assay can be used to determine candidate agents which interfere with binding of BIC to its binding partner. "Binding interference", or grammatical equivalents, as used herein means that native binding of the BIC protein differs in the presence of the candidate agent. The binding can be eliminated or can be with a reduced affinity. In one embodiment, interference is caused by, for example, a conformational change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the BIC protein and thus is capable of binding to, and potentially modulating, the activity of the BIC protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the BIC protein with a higher affinity. Thus, if the candidate bioactive agent is labeled, the presence of the label on the support, coupled with a lack of competitor binding, may indicate that the candidate agent is capable of binding to the BIC protein.

In an especially preferred embodiment, binding and binding interference assays are done using BIC which is inserted into a cell membrane. Preferably the BIC protein comprises four transmembrane domains, and binding of candidate agent or binding partner to an exposed surface of the BIC protein, on either side of the membrane, corresponding to an intracellular or extracellular region where the membrane is a plasma membrane, is determined. Binding of candidate agent or binding partner to a transmembrane portion, membrane-imbedded portion, or juxtamembrane portion of BIC protein may also be done. For example, interference of binding of BIC protein to BIC protein or other cation channel subunit, where interaction occurs between one or more of these regions, may be determined.

In a preferred embodiment, the methods comprise differential screening to identity bioactive agents that are capable of modulating the activity of the BIC proteins. In one embodiment, the methods comprise combining a BIC protein and a competitor in a first sample. A second sample comprises a candidate bioactive agent, a BIC protein and a competitor. The binding of the competitor is determined for both samples, and a change, or difference in binding between the two samples indicates the presence of an agent capable of binding to the BIC protein and modulating its activity. That is, if the binding of the competitor is different in the second sample relative to the first sample, the agent is capable of binding to the BIC protein and modulating its activity.

Alternatively, a preferred embodiment utilizes differential screening to identify drug candidates that bind to the native BIC protein, but cannot bind to modified BIC proteins. The structure of the BIC protein may be modeled, and used in rational drug design to synthesize agents that interact with the extracellular face of the channel, the pore opening, the intracellular face of the channel, the gating portion of the channel, the selectivity determining portion of the channel, and particular protein interaction domains.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of a BIC protein may also be done. In a preferred embodiment, methods for screening for a bioactive agent capable of modulating the activity of a BIC protein comprise the steps of adding a candidate bioactive agent to a sample of a BIC protein and determining an alteration in the biological activity of the BIC protein. "Modulating the activity of a BIC protein" includes an increase in activity, a decrease in activity, or a change in the type or kind of activity present. Thus, in this embodiment, the candidate agent may bind to a BIC protein (although this may not be necessary), and should alter its biological or biochemical activity as defined herein. The methods include in vivo screening of cells for alterations in the presence, cellular distribution, subcellular distribution, activity or amount of BIC protein. A change in the kind or type of activity includes a change in cation conductance, and/or a change in cation selectivity.

By "BIC protein activity" or grammatical equivalents herein is meant at least one of the BIC protein's biological activities, including, but not limited to, modulation of leukocyte activation; modulation of lymphocyte activation; modulation of lymphocyte activation by antigen; modulation of B-lymphocyte activation by BCR stimulation; modulation of T-lymphocyte activation by TCR stimulation; modulation of B-cell differentiation; modulation of lymphocyte proliferation; modulation of IgM and IgG induction in B-lymphocytes; modulation of surface Ig, particularly surface IgM expression, in resting lymphocytes; modulation of CD23 expression induced by IL-4, CD40L, or IL-4 and CD40L in lymphocytes; modulation of immunoglobulin heavy chain gene promoter activity in lymphocytes; modulation of NFAT activity in lymphocytes; modulation of immunoglobulin secretion by B-lymphocytes; modulation of cytokine production in leukocytes; modulation of surface protein expression including CD23, CD69, CD80 and CD86 in lymphocytes; modulation of cation conductance, preferably selected from potassium, sodium, and calcium, modulation of membrane potential; modulation of transmembrane current; modulation of intracellular cation concentration, preferably selected from potassium, sodium, and calcium; modulation of intracellular calcium concentration in lymphocytes; modulation of intracellular calcium concentration change in response to antigen-receptor activation in lymphocytes; modulation of calcineurin activity in lymphocytes; modulation of calcineurin activity induction by antigen receptor activation in lymphocytes.

In a preferred embodiment, the activity of the BIC protein is decreased; in another preferred embodiment, the activity of the BIC protein is increased. Thus, bioactive agents that are antagonists are preferred in some embodiments, and bioactive agents that are agonists are preferred in other embodiments.

In an especially preferred embodiment, methods of screening for candidate bioactive agents capable of modulating the cation conductance of a BIC protein are provided. In a preferred embodiment, the method involves transcribing a BIC nucleic acid encoding a BIC protein, introducing a BIC transcript into a host cell capable of expressing BIC, preferably a Xenopus oocyte, allowing time for expression of the BIC transcript and insertion of BIC protein into the host cell membrane, and patch clamping a region of the membrane of the host cell comprising a BIC protein encoded by said transcript. The patch may be pulled from the cell, in an outside-out or an inside-out configuration, or whole cell recording may be done. Patch clamping is a well known method in the art, and is used in the present methods to determine how current varies in the presence of candidate agent. Methods for synthesizing cRNA in vitro are well known, and kits are commercially available for this purpose (see Ambion, Austin, Tex., mMESSAGE mMACHINE™, catalog number 1340). Methods for introducing cRNA into host cells, including Xenopus oocytes, are well known in the art. Methods using Xenopus oocytes to study the behaviour of channel proteins, including patch clamping techniques, are well known in the art (see Sumikawa et al., Methods Neurosci., 1:3045,1989; Bertil Hille, *Ionic Channels of Excitable Membranes*, 3rd Ed., 2001, Sunderland Mass., Sinauer Associates Inc. Voltage clamping and measuring of current may be done as is well known in the art.

In another preferred embodiment, intracellular recording on host cells expressing recombinant BIC nucleic acid encoding BIC protein is done in the presence of candidate agent, and a change in transmembrane potential in the presence of candidate agent is detected. Methods for intracellular recording are known to those of skill in the art; for example, see *Microelectrode Methods for Intracellular Recording and Ionophoresis*, 1981, R. D. Purves, New York, Academic Press Current clamping may also be done as is well known in the art. See also Bertil Hille, supra.

In another preferred embodiment, the membrane potential of host cells expressing recombinant BIC nucleic acid encoding BIC protein is measured using photodetection techniques. Particularly, voltage-sensitive dyes which bind the host cell membrane and change their emission properties in response to changes in membrane potential are used to detect alterations in membrane potential in the presence of candidate agents. Voltage sensitive dyes, and methods for using the same, are well known. For example, see RH 115, Molecular Probes, Eugene, Oreg., catalog no. R-1114.

For further discussion of intracellular recording, patch clamp recording, whole cell recording, see *The Axon Guide*, Axon Instruments, Foster City, Calif., 1993, R. Sherman-Gold, editor.

The terms "membrane potential", "transmembrane potential", and "potential difference" are used equivalently herein.

In another preferred embodiment, the intracellular concentration of cations in host cells expressing recombinant BIC nucleic acid encoding BIC protein is visualized using cation-sensitive dyes that change their emission properties in response to their interaction with cations. For example, calcium sensitive dyes are used to visualize changes in intracellular calcium. Calcium sensitive dyes and methods for using the same are well known in the art. Fore example, see Calcium Green™-1, Molecular Probes, Eugene, Oreg., catalog no. C-3011.

It will be appreciated that such photodetection techniques lend themselves to the use of a FACS machine for measurement. Further, cells may be sorted based on these parameters.

Screening for agents that modulate B-cell activation and T-cell activation may also be done.

In a preferred embodiment, the methods comprise determining the ability of a candidate agent to bind to BIC.

In a preferred embodiment, the methods comprise detecting binding of candidate agent to BIC protein, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

It will be understood that while agents that normally induce lymphocyte activation (i.e., activation agents) are used, the screening method is designed to identify agents that are capable of inhibiting lymphocyte activation. Accordingly, the presence of a bioactive agent that is capable of inhibiting lymphocyte activation may preclude activation of the lymphocyte by the activation agent. Such agents are nevertheless referred to herein as activation agents, and the step of contacting the cells with such an activation agent is frequently referred to herein as "inducing lymphocyte activation", even though a candidate bioactive agent may inhibit such activation by the agent. This nomenclature applies to the methods that follow as well.

Bioactive agents that inhibit lymphocyte activation in these assays are useful as immunosuppressants.

By immunosuppressant is meant an agent that suppresses the body's ability to react to an antigen.

In another preferred embodiment, the methods comprise determining the ability of a candidate agent to modulate the binding of BIC to a BIC binding partner.

In a preferred embodiment, the methods comprise detecting modulation of BIC protein binding to a BIC binding partner in the presence of candidate agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, anti-BIC antibody is used as BIC binding partner. In another preferred embodiment, the BIC binding partner used is a cation channel modulator or blocker. In another preferred embodiment, the BIC binding partner used is BIC, or other cation channel subunit.

By modulation of BIC protein binding to BIC binding partner is meant a detectable increase or decrease in binding as compared to binding in the absence of agent, or absence of binding.

Preferred cation channel modulators or blockers for use in the methods herein include, but are not limited to, the following: tetrodotoxin (TTX), saxitoxin (STX), tetraethylammonium ion (TEA), $Cs^+$, $Ba^+$, 4-aminopyridine and related small molecules, cocaine, procaine, $Mn^+$, $Sr^+$, tetrabutylammonium (TBA), N-methylglucamine, nifedipine or other 1,4-dihydropyridines, BAY K 8644, $Co^{2+}$, $Ni^{2+}$, $Cd^{2+}$, $Mn^{2+}$, $La^{3+}$, verapamil, D-600, nitrendipine, diltiazem, conotoxin, apamin, charybdotoxin, capsaicin, noxiustoxin, dendrotoxin, and $Rb^+$.

Bioactive agents that inhibit lymphocyte activation in these assays are useful as immunosuppressants.

As is known in the art, cation channels exhibit selectivity for particular cations. Cations which can be conducted by BIC are sometimes referred to herein as permeant. Cations which cannot be conducted by BIC are sometimes referred to herein as impermeant.

In another preferred embodiment, the methods comprise determining the ability of a candidate bioactive agent to modulate the activity of a BIC protein.

In a preferred embodiment, the methods comprise determining a change in cation conductance of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

By change in cation conductance is meant a determinable increase or decrease in the cation conductance of a membrane as compared to its cation conductance in the absence of agent.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

Bioactive agents that inhibit lymphocyte activation in these assays are useful as immunosuppressants.

In another preferred embodiment, the methods comprise detecting a change in membrane potential of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, membrane potential is measured by voltage sensitive dye.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

By change in membrane potential is meant a detectable change in membrane potential as compared to the membrane potential in the absence of agent.

Bioactive agents that inhibit lymphocyte activation in these assays are useful as immunosuppressants.

In another preferred embodiment, the methods comprise detecting a change in transmembrane current of a membrane comprising BIC in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

By change in transmembrane current is meant a detectable change in transmembrane current as compared to the transmembrane current in the absence of agent.

Bioactive agents that inhibit lymphocyte activation in these assays are useful as immunosuppressants.

In another preferred embodiment, the methods comprise detecting a change in intracellular or extracellular cation concentration, i.e., to one side or the other of a membrane comprising BIC, in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

In a preferred embodiment, the methods involve the use of a cation sensor, preferably a cation-sensitive dye.

In a preferred embodiment, the methods involve expressing a recombinant BIC nucleic acid in a cell.

In a preferred embodiment, the methods involve inducing overexpression of endogenous BIC in a cell.

By change in intracellular or extracellular cation concentration is meant a detectable change in intracellular or extracellular cation concentration as compared to the intracellular or extracellular cation concentration in the absence of agent.

Bioactive agents that inhibit lymphocyte activation in these assays are useful as immunosuppressants.

In a preferred embodiment, the methods comprise detecting binding of candidate agent to BIC protein, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL4, CD40L, and the combination of IL4 and CD40L.

Bioactive agents that inhibit CD23 induction in these assays are useful as immunosuppressants.

In a preferred embodiment, the methods comprise detecting modulation of the binding of BIC protein to a BIC binding partner in the presence of candidate agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

Bioactive agents that inhibit CD23 induction in these assays are useful as immunosuppressants.

In a preferred embodiment, the methods comprise determining a change in cation conductance of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

Bioactive agents that inhibit CD23 induction in these assays are useful as immunosuppressants.

In a preferred embodiment, the methods comprise detecting a change in membrane potential of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

Bioactive agents that inhibit CD23 induction in these assays are useful as immunosuppressants.

In a preferred embodiment, the methods comprise detecting a change in transmembrane current of a membrane comprising BIC in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, whole cell recording is done.

In a preferred embodiment, patch clamp recording is done.

In a preferred embodiment, the methods involve expressing a recombinant BIC nucleic acid in a cell.

In a preferred embodiment, the methods involve inducing overexpression of endogenous BIC in a cell.

Bioactive agents that inhibit CD23 induction in these assays are useful as immunosuppressants.

In a preferred embodiment, the methods comprise detecting a change in intracellular or extracellular cation concentration, to one side or the other of a membrane comprising BIC, in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In a preferred embodiment, the methods involve the use of a cation sensor, preferably a cation-sensitive dye.

In a preferred embodiment, the methods involve expressing a recombinant BIC nucleic acid in a cell.

In a preferred embodiment, the methods involve inducing overexpression of endogenous BIC in a cell.

Bioactive agents that inhibit CD23 induction in these assays are useful as immunosuppressants.

In a preferred embodiment, the methods comprise detecting binding of candidate agent to BIC protein, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise detecting modulation of the binding of BIC protein to a BIC binding partner in the presence of candidate agent, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise determining a change in cation conductance of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in membrane potential of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in transmembrane current of a membrane comprising BIC in the presence of candidate bioactive agent, contacting the candidate bioactive agent to a resting B-lymphocyte, and determining the level of surface Ig expression, preferably surface IgM expression, in the cell.

In a preferred embodiment, the methods comprise detecting a change in intracellular or extracellular cation concentration, i.e., to one side or the other of a membrane comprising BIC, in the presence of candidate bioactive agent, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods involve expressing a recombinant BIC nucleic acid in a cell.

In a preferred embodiment, the methods involve inducing overexpression of endogenous BIC in a cell.

Agents that decrease surface Ig expression in resting B-cells are particularly preferred, and are useful as immunosuppressants.

In another preferred embodiment, the level of BIC mRNA expression, BIC protein expression, or BIC activity is used to screen for agents that modulate the level of BIC activity. Such agents are useful as immunosuppressants.

In a preferred embodiment, candidate bioactive agents used in these assays are small molecule chemical compounds, from about 100 to about 1500, more preferably about 100 to about 1200, more preferably about 100 to about 1000 more preferably about 200 to about 500 daltons.

In a preferred embodiment, a library of candidate bioactive agents is contacted to BIC protein.

In another preferred embodiment, a library of candidate bioactive agents is contacted to a population of cells comprising BIC protein.

In a preferred embodiment, determining lymphocyte activation in the methods herein comprises determining the level of expression of a surface marker which is associated with activation of the lymphocyte, in the presence of candidate agent. In a preferred embodiment, the level of surface marker expression is determined in the presence and absence of candidate agent. In a preferred embodiment, the surface marker is selected from the group consisting of CD40L, CD23, CD69, CD80 and CD86. In an especially preferred embodiment, the surface marker used is CD69 or CD23.

In another preferred embodiment, determining lymphocyte activation in the methods herein comprises determining the level of activity of a promoter in the presence of candidate agent, which activity correlates with lymphocyte activation in the absence of candidate agent. In a preferred embodiment, the level of promoter activity is determined in the presence and absence of candidate agent. In a preferred embodiment the promoter is an NFAT-responsive promoter, such as the IL-2 promoter. In an especially preferred embodiment, the promoter is the IgH promoter.

In a preferred embodiment, determining lymphocyte activation involves measuring lymphocyte activation using a FACS machine. In a preferred embodiment, lymphocytes are sorted by FACS on the basis of activation.

Similarly, in a preferred embodiment, determining surface Ig, preferably surface IgM expression in a resting B-lymphocyte is done using a FACS machine. In a preferred embodiment, lymphocytes are sorted by FACS on the basis of surface Ig expression.

In some embodiments, the methods involve determining B-lymphocyte activation by other means, which may also include the use of a FACS machine. As will be appreciated, lymphocyte activation as well as non-lymphocyte leukocyte activation and platelet activation can be determined in a number of ways. It will be appreciated that mechanisms of leukocyte activation and methods for determining activation are known (see for example Kay, Immunol. Invest. 17:679–705, 1988; Lukacs et. al., Chem. Immunol. 72:102–120,1999; Metcalf et. al., Physiol. Rev. 77:1033–1079, 1997; Hematol. Oncol. Clin. North Am. 4:1–26, 1990; Brass et. al., Adv. Exp. Med. Biol., 344:17–36, 1993; Brass et. al., Thromb. Haemost., 70:217–223, 1993; *Cellular and Molecular Immunology*, Abbas et. al., W. B. Saunders, ISBN 0-7216-3032-4, Chapters 7, 9, 12, and 14). Particularly relevant are the methods disclosed by Holland et al., J. Exp. Med., 194:1263–1276, 2001, expressly incorporated herein by reference.

In some embodiments, indicators of lymphocyte activation are used. There are a number of parameters that may be evaluated or assayed to determine lymphocyte activation, including, but not limited to, IgH promoter activity, NFAT activity, lg secretion, IgG and IgM production, lymphocyte proliferation, expression cell surface markers correlated with lymphocyte activation, cytokine production, calcium flux; release of calcium from intracellular stores, amount of SYK protein, level of SYK protein ubiquitination, SYK protein tyrosine kinase activity, and IL-2 expression. These parameters may be assayed and used as indicators to evaluate the effect of candidate drug agents on lymphocyte activation. In this manner, rapid, accurate screening of candidate agents may be performed to identify agents that modulate lymphocyte activation.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colorectal, leukemia, brain, etc. More preferable cell types include Jurkat cells (T-lymphocyte cell line) and the Ig(+) and IgM secreting B-cell lines CL-01, LA350, BJAB, and CA46. Primary cells are also preferred, including peripheral blood lymphocytes (PBLs) and peripheral blood mononuclear cells (PBMCs). Ramos cells (B-cell cell line) are also preferred.

In the methods provided herein requiring the use of lymphocytes, lymphocyte-like cells or lymphocyte cell lines, such as those described above, or primary lymphocytes may be used.

Preferred cell surface markers useful as indicators of lymphocyte activation in the methods herein exhibit low background expression in the absence of lymphocyte activation. Especially preferred cell surface markers include CD40L, CD23, CD69, CD80, CD86. CD69 and CD23 are especially preferred.

Agents that recognize such surface molecules (e.g. antibodies) can be used as an affinity ligand, and attached to a solid support such as a bead, a surface, etc., and used to pull out cells that are undergoing T-cell and B-cell activation. Similarly, these agents can be coupled to a fluorescent dye such as PerCP, and then used as the basis of a fluorescence-activated cell sorting (FACS) separation.

FACS analysis can be used in conjunction with antibodies recognizing lymphocyte surface markers that are correlated with lymphocyte activation. FACS analysis is used to sort cells based on the expression of these markers to detect unstimulated and stimulated lymphocytes. In a preferred embodiment, sorted lymphocytes are used to retrieve candidate bioactive agents introduced thereto.

In a preferred embodiment, IgH promoter activity and NFAT activity are measured using lymphocyte clones comprising an IgH promoter or an NFAT-responsive promoter (such as IL-2 promoter) operably linked to a reporter gene. For example, a surface Ig(+), IgM secreting B-cell line such as the BJAB, CL-01, CA46, or LA350 cell line is transfected with a construct comprising GFP/2a/TK fusion under the control of an IgH promoter, E$\mu$ and 3'$\alpha$ enhancer elements. Stable transfectants (referred to herein as immunoglobulin heavy chain reporter cell lines) are selected and maintained in gancyclovir. Preferred immunoglobulin heavy chain reporter cell lines for use in the present invention exhibit low background GFP expression and strong basal activity and/or inducible activity in the presence of positive control. Such cell lines can be generated with the use of retroviral constructs.

Release of calcium from intracellular calcium stores may be assayed using membrane permeant vital calcium sensing fluorescent dyes, as are well known in the art.

A preferred embodiment utilizes a cell proliferation assay. For example, B-cells proliferate when activated. By "proliferation assay" herein is meant an assay that allows the determination that a cell population is either proliferating, i.e. replicating, or not proliferating.

In a preferred embodiment, the proliferation assay is a dye inclusion assay. A dye inclusion assay relies on dilution effects to distinguish between proliferating and non-proliferating cells. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

The rate of loss of fluorescence is indicative of the rate of proliferation. An increase in proliferation rate above that of unstimulated cells is indicative of B-cell activation.

Generally, the introduction of the inclusion dye may be done in one of two ways. Either the dye cannot passively enter the cells (e.g. it is charged), and the cells must be treated to take up the dye; for example through the use of an electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook; chapter 15 in particular.

In general, inclusion dyes are provided to the cells at a concentration ranging from about 100 ng/ml to about 5 $\mu$g/ml, with from about 500 ng/ml to about 1 $\mu$g/ml being preferred. A wash step may or may not be used. In a preferred embodiment, a candidate bioactive agent is combined with the cells as described herein. The cells and the inclusion dye are incubated for some period of time, to allow cell division and thus dye dilution.

Without being bound by theory, it is recognized herein that BIC proteins are involved in the regulation of signal transduction in lymphocytes. Particularly, BIC proteins are recognized herein as being critical regulators of B-cell and T-cell activation. As discussed above, the activation of specific signaling pathways in lymphocytes determines the quality, magnitude, and duration of immune responses. In transplantation, acute and chronic inflammatory diseases, and autoimmunity, it is these pathways that are responsible for the induction, maintenance and exacerbation of undesirable lymphocyte responses.

Accordingly, in one aspect, the invention provides compositions and methods for the treatment of lymphocyte activation disorders and platelet activation or proliferation disorders, as described below.

In a preferred embodiment, the present invention provides BIC proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant. Among these diseases are those listed in FIG. 4.

In another preferred embodiment, the present invention provides BIC proteins and nucleic acids, as well as agents that bind to them and/or modulate their activity, including and preferably small molecule chemical compositions as discussed herein, which are useful in the treatment of physiological states that are characterized by or lead to the presentation of some or all symptoms characteristic of acute inflammatory disease, chronic inflammatory disease, autoimmune disease, or response to transplantation.

It will be understood that these diseases and states may or may not be associated with altered BIC activity. That is, BIC compositions (proteins, nucleic acids, anti-BIC antibodies, agonists, antagonists) find use in the prevention and/or treatment of diseases and states which do not have BIC dysregulation or dysfunction as a molecular basis, but still involve lymphocyte activation and/or proliferation. That is, a disease or state need not be associated with BIC activity for the present compositions and methods to be useful in preventing or treating it. Many autoimmune diseases fall into this category.

In another preferred embodiment, the present invention provides BIC proteins and nucleic acids, as well as agents that bind to them and/or modulate their activity, including and preferably small molecule chemical compositions as discussed herein, which are useful as prophylactics for the prevention of acute inflammatory disease, chronic inflammatory disease, autoimmune disease, and response to transplantation.

In a preferred embodiment, the present invention provides BIC proteins and nucleic acids, as well as agents that bind to them and/or modulate their activity, including and preferably small molecule chemical compositions as discussed herein, which are useful as prophylactics for the prevention of physiological states that are characterized by or lead to the presentation of some or all symptoms characteristic of acute inflammatory disease, chronic inflammatory disease, autoimmune disease, or response to transplantation.

In a preferred embodiment, BIC proteins and nucleic acids provided herein are useful for the inhibition of antigen receptor-induced lymphocyte activation, as characterized by the induction of CD69 and other markers of activation. Particularly useful for this purpose is a BIC protein comprising the amino acid sequence set forth by residues 21–273 or 1–273 in SEQ ID NO:2.

In an especially preferred embodiment, BIC proteins and nucleic acids provided herein are useful for the inhibition of immunoglobulin production by B lymphocytes that normally results from BCR activation by antigen. Particularly useful for this purpose is a BIC protein comprising the amino acid sequence set forth by residues 21–273 or 1–273 in SEQ ID NO:2.

Without being bound by theory, BIC proteins, being modulators of signal transduction in lymphocytes, particularly signal transduction events underlying lymphocyte activation, are involved in the regulation of proliferation of lymphocytes, and have utility as modulators of lymphocyte proliferation. Further, disorders associated with BIC dysfunction or dysregulation include lymphocyte proliferation disorders, such as leukemias and lymphomas.

Accordingly, in a preferred embodiment, the present invention provides BIC proteins and nucleic acids, as well as agents capable of binding to them or modulating their activity, including and preferably small molecule chemical compositions as discussed herein, which are useful in the treatment of disorders involving T-cell and B-cell proliferation, including leukemias and lymphomas.

It is recognized in the art that signaling pathways involved in the regulation of cell proliferation frequently participate in, directly or indirectly, the regulation of cell survival and programmed cell death. It is further recognized in the art that the dysregulation of mechanisms of programmed cell death can lead to cancer, particularly in lymphocytes. For example, overexpression of Bcl-2, which promotes cell survival through the inhibition of apoptotic processes, is thought to be responsible for the survival of excessive numbers of lymphocytes in a form of lymphoma (Reed et al., Science, 236:1295–1299, 1987; Tsujimoto et al., Science, 228:1440–1443, 1985).

Accordingly, the present invention provides BIC proteins and nucleic acids, as well as agents capable of binding to them and/or modulating their activity, including and preferably small molecule chemical compositions as discussed herein, which are useful in the treatment of disorders involving T-cell and B-cell survival and programmed cell death, including cancer.

The proteins and nucleic acids provided herein can also be used for screening purposes wherein the protein-protein interactions of the BIC proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463. A preferred system is described in Ser. Nos. 09/050,863, filed Mar. 30, 1998 and 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a BIC protein or a portion thereof, and the other encodes a test candidate. Only if the two expression products bind to one another will an indicator, such as a fluorescent protein, be expressed. Expression of the indicator indicates when a test candidate binds to the BIC protein, and identifies the candidate as being part of a T-cell or B-cell BIC signaling pathway. A test candidate so identified may then be used as bait to identify binding proteins that are also identified as being part of a T-cell or B-cell BIC signaling pathway. Additionally, BIC proteins may be used to identify new baits, or agents that bind to BIC proteins. Additionally, the two-hybrid system can be used wherein a test candidate is added in addition to the bait and the BIC protein encoding nucleic acids to determine agents which interfere with the binding of bait to the BIC protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli. etc., that may contribute to conditions which can effect protein-protein interactions.

Assays involving binding such as the two-hybrid system may take into account non-specific binding proteins (NSB).

Expression in various cell types, and assays for BIC activity are described above. The activity assays can be performed to confirm the activity of BIC proteins which have already been identified by their sequence identity/ similarity to BIC, as well as to further confirm the activity of lead compounds identified as modulators of BIC activity.

The components provided herein for the assays provided herein may also be combined to form kits. The kits can be based on the use of BIC proteins and/or nucleic acids encoding BIC proteins. In one embodiment, other components are provided in the kit. Such components include one or more of packaging, instructions, antibodies, and labels. Additional assays such as those used in diagnostics are further described below.

Bioactive agents may be identified by the methods provided herein. Compounds with pharmacological activity are able to enhance or interfere with the activity of the BIC protein. The compounds having the desired pharmacological activity may be administered in a physiologically acceptable carrier to a host, as further described below.

The present discovery relating to the role of BIC proteins in leukocytes thus provides methods for inducing or preventing leukocyte activation, preferably lymphocyte activation. In a preferred embodiment, the BIC proteins, and particularly BIC protein fragments, are useful in the study or treatment of conditions which involve dysfunction or dysregulation of BIC protein activity, i.e. to diagnose, treat or prevent BIC associated disorders. "BIC associated disorders" or "disease states" or "physiological states associated with BIC dysfunction or dysregulation" include conditions involving insufficient, excessive, and inappropriate BIC activity. Among these disorders are lymphocyte activation and proliferation disorders.

Thus, in one embodiment, methods for regulating lymphocyte activation in cells or organisms are provided. In one embodiment, the methods comprise administering to a cell or individual, a BIC protein in a therapeutic amount.

In one embodiment, the activity of BIC is increased. As will be appreciated by those in the art, this may be accomplished in any number of ways. In a preferred embodiment, the activity of BIC is increased by increasing the amount of BIC in the cell, for example by overexpressing the endogenous BIC or by administering a gene encoding a BIC protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, BIC activity may be increased by administering an agent determined to increase BIC activity r expression by the methods provided herein.

In one embodiment, the activity of BIC is decreased. As will be appreciated by those in the art, this may be accomplished in any number of ways. In a preferred embodiment, the activity of BIC is decreased by decreasing the amount of BIC mRNA in the cell, for example by expressing BIC antisense RNA. Double stranded nucleic acids for use in RNA interference (see Caplan, Trends in Biotechnology, 20: 49–51, 2002) are also preferred for this purpose. Alternatively, endogenous BIC activity is decreased by administering a dominant negative BIC protein or a gene encoding a dominant negative BIC protein. Alternatively, endogenous BIC activity is decreased by administering anti-BIC antibody or a gene encoding anti-BIC antibody or an epitope recognizing portion thereof. Particularly preferred are intrabodies, which are useful for the inhibition of intracellular BIC protein in situ. Known gene-therapy techniques may be used to administer these agents. In a preferred embodiment, the gene therapy techniques involve incorporation of the exogenous gene into the host genome using enhanced homologous recombination (EHR), for example as described in PCT/US93/03868, hereby incorporated by reference in its entirety. Alternatively, BIC activity is decreased by administering an agent determined to decrease BIC activity or expression by the methods provided herein.

It appears that BIC protein is an important protein in leukocyte activation, particularly lymphocyte activation. Accordingly, disorders based on mutant or variant BIC genes may be determined. In one embodiment, the invention provides methods for identifying cells containing variant BIC genes comprising determining all or part of the sequence of at least one endogenous BIC gene in a cell. As will be appreciated by those in the art, this may be done using any number of sequencing techniques. In a preferred embodiment, the invention provides methods of identifying the BIC genotype of an individual comprising determining all or part of the sequence of at least one BIC gene of the individual. This is generally done in at least one tissue of the individual, and may include the evaluation of a number of tissues or different samples of the same tissue. The method may include comparing the sequence of the sequenced BIC gene to a known BIC gene, i.e. a wild-type gene.

The sequence of all or part of the BIC gene can then be compared to the sequence of a known BIC gene to determine if any differences exist. This can be done using any number of known sequence identity programs, such as Bestfit, etc. In a preferred embodiment, the presence of a difference in the sequence between the BIC gene of the patient and the known BIC gene is indicative of a disease state or a propensity for a disease state, particularly a lymphocyte activation disorder (including proliferation disorders).

In one embodiment, the invention provides methods for diagnosing a BIC related condition in an individual. The methods comprise measuring the activity of BIC in a tissue from the individual or patient, which may include a measurement of the amount or specific activity of a BIC protein. This activity is compared to the activity of BIC from either an unaffected second individual or from an unaffected tissue from the first individual. When these activities are different, the first individual may be at risk for a BIC associated disorder. In this way, for example, monitoring of various disease conditions may be done by monitoring the absolute BIC activity in a sample or the specific activity of a BIC protein from a sample. Similarly, activity levels may correlate with prognosis.

In a preferred embodiment, BIC activity levels are determined in lymphocytes of an affected individual.

In one aspect, the expression levels of BIC genes (encoding BIC proteins) are determined in different patient samples or cells for which either diagnostic or prognostic information is desired. Gene expression monitoring is done on genes encoding BIC proteins. In one aspect, the expression levels of BIC genes are determined for different cellular states, such as normal cells and activated cells. By comparing BIC gene expression levels in cells in different states, information including both up- and down-regulation of BIC genes is obtained, which can be used in a number of ways.

For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising probes that determine the presence of BIC genes, which biochips can be used in these screens. These methods can also be done on the protein basis; that is, BIC protein expression levels can be evaluated for diagnostic and prognostic purposes or to screen candidate agents for their effects on BIC protein expression. ELISA methods, and array-based protein detection methods are know to those skilled in the art.

In a preferred embodiment, BIC expression levels are determined in lymphocytes in the presence of candidate agents. This determination is done to screen for agents capable of modulating BIC expression, which find use as immunosuppressants.

In a preferred embodiment, nucleic acid probes to BIC nucleic acids and their complements are made. The nucleic acid probes are designed to be substantially complementary to BIC nucleic acids, i.e., the target sequence, such that hybridization of the target sequence and the probe occurs. As outlined below, this complementarity need not be perfect; there may be any number of base pair mismatches which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95135505; U.S. Pat. Nos. 5,700,637 and 5,445,934; and references cited within, all of which are expressly incorporated by reference; these methods of attachment form the basis of the Affimetrix Gene-ChipT™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, a normal versus an apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques, such as by use of Affymetrix Gene-Chip™ expression arrays, Lockhart, Nature Biotechnology 14:1675–1680 (1996), hereby expressly incorporated by reference. Other techniques include, but are not limited to, quantitative reverse transcriptase PCR, Northern analysis and RNase protection.

Though discussed above with respect to transcripts, it will be appreciated by those in the art that this may be done by evaluation at either the gene transcript, or the protein level; that is, the amount of gene expression may be monitored using nucleic acid probes to the DNA or RNA gene transcript, and the quantification of gene expression levels, or, alternatively, the final gene product itself (protein) can be monitored, for example through the use of antibodies to the BIC protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a BIC protein is detected by binding the digoxygenin with an anti-digoxygenin secondary antibody and exposing to nitro blue tetrazolium and 5-bromo4-chloro-3-indoyl phosphate.

In another preferred method, expression of BIC protein is determined using in situ imaging techniques employing antibodies to BIC proteins. In this method cells are contacted with from one to many antibodies to the BIC protein(s). Following washing to remove non-specific antibody binding, the presence of the antibody or antibodies is detected. In one embodiment the antibody is detected by incubating with a secondary antibody that contains a detectable label. In another method the primary antibody to the BIC protein(s) contains a detectable label. In another preferred embodiment each one of multiple primary antibodies contains a distinct and detectable label. This method finds particular use in simultaneous screening for a plurality of BIC proteins. The label may be detected in a fluorometer which has the ability to detect and distinguish emissions of different wavelengths. Labels may be detected using a fluorescence microscope which has multiple fluorescence channels. In addition, a fluorescence activated cell sorter (FACS) can be used in this method. As will be appreciated by one of ordinary skill in the art, numerous other histological imaging techniques are useful in the invention and the antibodies can also be used in ELISA, immunoblotting (Western blotting), immunoprecipitation, BIACORE technology, and the like.

In one embodiment, the BIC proteins of the present invention may be used to generate polyclonal and monoclonal antibodies to BIC proteins, which are useful as described herein. Similarly, the BIC proteins can be coupled, using standard technology, to affinity chromatography columns. These columns may then be used to purify BIC antibodies. In a preferred embodiment, the antibodies are generated to epitopes unique to the BIC protein; that is, the antibodies show little or no cross-reactivity to other proteins. These antibodies find use in a number of applications. For example, the BIC antibodies may be coupled to standard affinity chromatography columns and used to purify BIC proteins as further described below. The antibodies may also be used as blocking polypeptides, as outlined above, since they will specifically bind to the BIC protein.

The anti-BIC protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the BIC protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-BIC protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the BIC protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against BIC protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-conibining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Alternatively, intrabodies may be prepared that are capable of binding to BIC intracellularly. Wirtz et al., *Prot. Sci.* 8(11):2245–50 (1999); Ohage etal. *J. Mol. Biol.* 291(5): 1129–34 and Ohage et al. *J. Boil. Chem.* 291(5): 1119–28 (1999), the disclosures of which are expressly incorporated by reference herein. Preferably such intrabodies are lipid soluble and lack a constant region. Intrabodies are particularly useful for the treatment of lymphocyte activation disorders.

The anti-BIC protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

Bispecific antibodies are monoclonal, preferably human or humanized, antibodies that have binding specificities for at least two different antigens. In the present case, one of the binding specificities is for the BIC protein, the other one is for any other antigen, and preferably for a cell-surface protein or receptor or receptor subunit, preferably for a protein on the surface of a dysregulated or dysfunctional lymphocyte.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl4-mercaptobutyrimidate and those disclosed, for example, in U.S. Pat. No. 4,676,980.

The anti-BIC protein antibodies of the invention have various utilities. For example, anti-BIC protein antibodies may be used in diagnostic assays for a BIC protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-BIC protein antibodies also are useful for the affinity purification of BIC protein from recombinant cell culture or natural sources. In this process, the antibodies against BIC protein are immobilized on a suitable support, such a Sephadex resin or filter paper, using methods well known in the art. The immobilized antibody then is contacted with a sample containing the BIC protein to be purified, and thereafter the support is washed with a suitable solvent that will remove substantially all the material in the sample except the BIC protein, which is bound to the immobilized antibody. Finally, the support is washed with another suitable solvent that will release the BIC protein from the antibody.

The anti-BIC protein antibodies may also be used in treatment. In one embodiment, the genes encoding the antibodies are provided, such that the antibodies bind to and modulate the BIC protein within the cell.

In one embodiment, a therapeutically effective dose of a BIC protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for BIC protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus the methods are applicable to both human therapy and veterinary applications. In the preferred embodiment the patient is a mammal, and in the most preferred embodiment the patient is human.

The administration of the BIC protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100% wt.

The pharmaceutical compositions of the present invention comprise a BIC protein, agonist or antagonist (including antibodies and bioactive agents as described herein, most preferably small molecule chemical compositions as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of BIC protein related disorders with an antibody raised against a BIC protein. Immunotherapy may also be used to treat lymphocyte activation disorders not associated with BIC, but treatable by BIC modulation.

The invention also includes the use of BIC protein compositions, BIC agonists, or BIC antibodies, in the preparation of a medicament for the treatment of lymphocyte activation disorders and lymphocyte proliferation disorders.

All references cited herein are expressly incorporated by reference in their entirety. Moreover, all sequences displayed, cited by reference or accession number in the references are incorporated by reference herein.

We claim:

1. A method of screening for an immunosuppressant, comprising:
   a) combining a candidate bioactive agent, and a cell comprising a BIC protein;
   b) detecting a change in the membrane potential of said cell in the presence of said candidate bioactive agent;
   c) contacting said candidate bioactive agent to a lymphocyte;
   d) inducing activation of said lymphocyte; and
   e) determining the activation of said lymphocyte in the presence of said candidate bioactive agent;
   wherein said BIC protein comprises four transmembrane domains and an amino acid sequence having at least about 95% identity to the amino acid sequence set forth in SEQ ID NO:2 or 4, and wherein a decrease in the activation of said lymphocyte in the presence of said candidate bioactive agent indicates that said candidate bioactive agent is an immunosuppressant.

2. The method according to claim 1, wherein said BIC protein comprises the amino acid sequence set forth in SEQ ID NO:2 or 4.

3. The method according to claim 1, wherein detecting a change in the membrane potential of said cell is done using a voltage-sensitive dye.

4. A method of screening for an immunosuppressant, comprising:
   a) providing a cell comprising a membrane, wherein said membrane comprises a BIC protein;
   b) patch clamping a portion of said membrane which comprises at least one BIC protein;
   c) contacting said BIC protein with a candidate bioactive agent;
   d) detecting a change in the current conductance of said BIC protein in the presence of said candidate bioactive agent;
   e) contacting said candidate bioactive agent to a lymphocyte;
   f) inducing activation of said lymphocyte; and
   g) determining the activation of said lymphocyte in the presence of said candidate bioactive agent;
   wherein said BIC protein comprises four transmembrane domains and an amino acid sequence having at least about 95% identity to the amino acid sequence set forth in SEQ ID NO:2 or 4, and wherein a decrease in the activation of said lymphocyte in the presence of said candidate bioactive agent indicates that said candidate bioactive agent is an immunosuppressant.

5. The method according to claim 4, wherein said BIC protein comprises the amino acid sequence set forth in SEQ ID NO:2 or 4.

6. A method of screening for an immunosuppressant, comprising:
   a) combining a candidate bioactive agent, a BIC protein, and a BIC binding partner;
   b) detecting modulation of the binding of paid BIC protein to said BIC binding partner in the presence of said candidate bioactive agent;
   c) contacting said candidate bioactive agent to a lymphocyte;
   d) inducing activation of said lymphocyte; and
   e) determining the activation of said lymphocyte in the presence of said candidate bioactive agent;
   wherein said BIC protein comprises four transmembrane domains and an amino acid sequence having at least about 95% identity to the amino acid sequence set forth in SEQ ID NO:2 or 4, wherein said BIC protein will bind to said BIC binding partner in the absence of said candidate bioactive agent, and wherein a decrease in the activation of said lymphocyte in the presence of said candidate bioactive agent indicates that said candidate bioactive agent is an immunosuppressant.

7. The method according to claim 6, wherein said BIC binding partner is an anti-BIC antibody.

8. The method according to claim 6, wherein said BIC protein comprises the amino acid sequence set forth in SEQ ID NO:2 or 4.

9. A method of screening for an immunosuppressant, comprising:
   a) combining a candidate bioactive agent, and a BIC protein;
   b) detecting binding of said BIC protein to said candidate bioactive agent;
   c) contacting said candidate bioactive agent to a lymphocyte;
   d) inducing activation of said lymphocyte; and
   e) determining the activation of said lymphocyte in the presence of said candidate bioactive agent;
   wherein said BIC protein comprises four transmembrane domains and an amino acid sequence having at least about 95% identity to the amino acid sequence set forth in SEQ ID NO:2 or 4, and wherein a decrease in the activation of said lymphocyte in the presence of said candidate bioactive agent indicates that said candidate bioactive agent is an immunosuppressant.

10. The method according to claim 9, wherein said BIC protein comprises the amino acid sequence set forth in SEQ ID NO:2 or 4.

11. The method according to any of claims 1–10, wherein said candidate bioactive agent is a small molecule chemical compound from about 200 to about 500 daltons in size.

12. The method according to any of claims 1–10, wherein said lymphocyte is a B lymphocyte.

13. The method according to claim 12, wherein inducing the activation of said B lymphocyte is done by activating the B cell receptor (BCR).

14. The method according to any of claims 1–10, wherein said lymphocyte is a T lymphocyte.

15. The method according to claim 14, wherein inducing the activation of said T lymphocyte is done by activating the T cell receptor (TCR).

16. The method according to claim 12, wherein determining the activation of said lymphocyte comprises determining the activity of the immunoglobulin heavy chain gene (IgH) promoter.

17. The method according to claim 12, wherein determining the activation of said lymphocyte comprises determining the expression of CD69.

18. The method according to claim 14, wherein determining the activation of said lymphocyte comprises determining the expression of CD69.

19. The method according to any of claims 1, 4, 6, and 9, wherein a library of candidate bioactive agents is combined with said BIC protein.

20. The method according to any of claims 1, 4, 6, and 9, wherein determining the activation of said lymphocyte involves sorting said lymphocyte by FAGS.

* * * * *

SEQUENCE LISTING

<160> NUMBER OF SEQ ID NOS: 4

<210> SEQ ID NO 1
<211> LENGTH: 1650
<212> TYPE: DNA
<213> ORGANISM: Homo sapiens
<220> FEATURE:
<221> NAME/KEY: CDS
<222> LOCATION: (133)..(954)
<223> OTHER INFORMATION:

<400> SEQUENCE: 1

```
gcggtgaccg cgggcgggtg gggcgccggg tgaagaaacc aagacgcaga gaggccaagc        60
cccttgcctt gggtcacaca gccaaaggag gcagagccag aactcacaac cagatccaga       120
ggcaacaggg ac atg gcc acc tgg gac gaa aag gca gtc acc cgc agg gcc       171
              Met Ala Thr Trp Asp Glu Lys Ala Val Thr Arg Arg Ala
                1               5                  10 aag gtg gct ccc gct gag agg atg agc aag ttc tta agg cac ttc acg       219
Lys Val Ala Pro Ala Glu Arg Met Ser Lys Phe Leu Arg His Phe Thr
     15                  20                  25 gtc gtg gga gac gac tac cat gcc tgg aac atc aac tac aag aaa tgg       267
Val Val Gly Asp Asp Tyr His Ala Trp Asn Ile Asn Tyr Lys Lys Trp
 30                  35                  40                  45 gag aat gaa gag gag gag gag gag gag gag cag cca cca ccc aca cca       315
Glu Asn Glu Glu Glu Glu Glu Glu Glu Glu Gln Pro Pro Pro Thr Pro
```

```
                50                  55                  60
gtc tca ggc gag gaa ggc aga gct gca gcc cct gac gtt gcc cct gcc     363
Val Ser Gly Glu Glu Gly Arg Ala Ala Ala Pro Asp Val Ala Pro Ala
                65                  70                  75 cct ggc ccc gca ccc agg gcc ccc ctt gac ttc agg ggc atg ttg agg     411
Pro Gly Pro Ala Pro Arg Ala Pro Leu Asp Phe Arg Gly Met Leu Arg
            80                  85                  90 aaa ctg ttc agc tcc cac agg ttt cag gtc atc atc atc tgc ttg gtg     459
Lys Leu Phe Ser Ser His Arg Phe Gln Val Ile Ile Ile Cys Leu Val
        95                  100                 105 gtt ctg gat gcc ctc ctg gtg ctt gct gag ctc atc ctg gac ctg aag     507
Val Leu Asp Ala Leu Leu Val Leu Ala Glu Leu Ile Leu Asp Leu Lys
110                 115                 120                 125 atc atc cag ccc gac aag aat aac tat gct gcc atg gta ttc cac tac     555
Ile Ile Gln Pro Asp Lys Asn Asn Tyr Ala Ala Met Val Phe His Tyr
                130                 135                 140 atg agc atc acc atc ttg gtc ttt ttt atg atg gag atc atc ttt aaa     603
Met Ser Ile Thr Ile Leu Val Phe Phe Met Met Glu Ile Ile Phe Lys
            145                 150                 155 tta ttt gtc ttc cgc ctg gag ttc ttt cac cac aag ttt gag atc ctg     651
Leu Phe Val Phe Arg Leu Glu Phe Phe His His Lys Phe Glu Ile Leu
        160                 165                 170 gat gcc gtc gtg gtg gtg gtc tca ttc atc ctc gac att gtc ctc ctg     699
Asp Ala Val Val Val Val Val Ser Phe Ile Leu Asp Ile Val Leu Leu
175                 180                 185 ttc cag gag cac cag ttt gag gct ctg ggc ctg ctg att ctg ctc cgg     747
Phe Gln Glu His Gln Phe Glu Ala Leu Gly Leu Leu Ile Leu Leu Arg
190                 195                 200                 205 ctg tgg cgg gtg gcc cgg atc atc aat ggg att atc atc tca gtt aag     795
Leu Trp Arg Val Ala Arg Ile Ile Asn Gly Ile Ile Ile Ser Val Lys
                210                 215                 220 aca cgt tca gaa cgg caa ctc tta agg tta aaa cag atg aat gta caa     843
Thr Arg Ser Glu Arg Gln Leu Leu Arg Leu Lys Gln Met Asn Val Gln
            225                 230                 235 ttg gcc gcc aag att caa cac ctt gag ttc agc tgc tct gag aag gaa     891
Leu Ala Ala Lys Ile Gln His Leu Glu Phe Ser Cys Ser Glu Lys Glu
        240                 245                 250 caa gaa att gaa aga ctt aac aaa cta ttg cga cag cat gga ctt ctt     939
Gln Glu Ile Glu Arg Leu Asn Lys Leu Leu Arg Gln His Gly Leu Leu
    255                 260                 265 ggt gaa gtg aac tag acccggacca gctcccctca aaagaagac actgtctcat      994
Gly Glu Val Asn
270 gggcctgtgc tgtcacgaga ggaacagctg cccctcctgg gccgcttggt gagaggtttg   1054 gtttgatacc tctgcctccc tcctgccagc atggattctg ggtggacaca gccttgtgga   1114 aggtccagta ccaccaagag ctgcccatcc actcccaccc cacactgtat caaatgtatc   1174 acattttctc atgttgaaca ctttagcctt aattgaaaat gagcaacaaa gctggacaat   1234 tgctagttgt atataaaatt taatctcacc gaatgtacag ttttcaaatt tcacgtgtat   1294 attaaggaac tgatgcatct gagcattctg aagaaagaa aaagaagcta ctttagctgc    1354 cacccccattc tagaaaagtc tcttattttc aagctgttct aaatagcttc gtctcagttt  1414 ccccaaaagg ggtacccagg cccctcctct gtgtgcccca gctgcatcag ccagcttcta   1474 ggtggctcca ttgttttctg ccacctgaca acatttttcc tcaattactg tacaactact   1534 gtataaaata aaacaactac tgtataaaat aaactctctc ttttccctgg aaaaaaaaa    1594 aaaaaaaaa aaaaaaaaa aaaaaaaa aaaaaaaaa aaaaaaaaa aaaaaa            1650
```

```
<210> SEQ ID NO 2
<211> LENGTH: 273
<212> TYPE: PRT
<213> ORGANISM: Homo sapiens

<400> SEQUENCE: 2

Met Ala Thr Trp Asp Glu Lys Ala Val Thr Arg Arg Ala Lys Val Ala
1               5                   10                  15

Pro Ala Glu Arg Met Ser Lys Phe Leu Arg His Phe Thr Val Val Gly
                20                  25                  30

Asp Asp Tyr His Ala Trp Asn Ile Asn Tyr Lys Lys Trp Glu Asn Glu
            35                  40                  45

Glu Glu Glu Glu Glu Glu Gln Pro Pro Thr Pro Val Ser Gly
        50                  55                  60

Glu Glu Gly Arg Ala Ala Ala Pro Asp Val Ala Pro Ala Pro Gly Pro
65                  70                  75                  80

Ala Pro Arg Ala Pro Leu Asp Phe Arg Gly Met Leu Arg Lys Leu Phe
                85                  90                  95

Ser Ser His Arg Phe Gln Val Ile Ile Ile Cys Leu Val Val Leu Asp
                100                 105                 110

Ala Leu Leu Val Leu Ala Glu Leu Ile Leu Asp Leu Lys Ile Ile Gln
            115                 120                 125

Pro Asp Lys Asn Asn Tyr Ala Ala Met Val Phe His Tyr Met Ser Ile
        130                 135                 140

Thr Ile Leu Val Phe Phe Met Met Glu Ile Ile Phe Lys Leu Phe Val
145                 150                 155                 160

Phe Arg Leu Glu Phe Phe His His Lys Phe Glu Ile Leu Asp Ala Val
                165                 170                 175

Val Val Val Val Ser Phe Ile Leu Asp Ile Val Leu Leu Phe Gln Glu
                180                 185                 190

His Gln Phe Glu Ala Leu Gly Leu Leu Ile Leu Leu Arg Leu Trp Arg
            195                 200                 205

Val Ala Arg Ile Ile Asn Gly Ile Ile Ile Ser Val Lys Thr Arg Ser
210                 215                 220

Glu Arg Gln Leu Leu Arg Leu Lys Gln Met Asn Val Gln Leu Ala Ala
225                 230                 235                 240

Lys Ile Gln His Leu Glu Phe Ser Cys Ser Glu Lys Glu Gln Glu Ile
                245                 250                 255

Glu Arg Leu Asn Lys Leu Leu Arg Gln His Gly Leu Leu Gly Glu Val
                260                 265                 270

Asn

<210> SEQ ID NO 3
<211> LENGTH: 2103
<212> TYPE: DNA
<213> ORGANISM: Homo sapiens
<220> FEATURE:
<221> NAME/KEY: CDS
<222> LOCATION: (745)..(1455)
<223> OTHER INFORMATION:

<400> SEQUENCE: 3
ctcagactac aggtgtgagc caccatgccc ggccttctcc tttaagtatt gttggcctca      60 cttttcccaac taaatggga gctcactaag aacaaaggct gttccttcat cttatactta    120
gtaccttgaa agggcctacc acacagtagg tggtcacgtg ttagtctgtt aggtcttttg    180
```

-continued

```
gattttctag gtagacaatc acatcgattg caaataatag tctttctctt ttcagtcttt     240
gtatttcttt tttcttgttt tattgcattg actgagctca tcagtgaaat gttgaatagt     300
agcaatgatg gagggcaccc caatcttatt atgctcaata ctcattaatt tatgcaatag     360
gaatgtaaag tacctactgc aggtcaaatc ctgtgcctgg ggataacagt gtaacacatt     420
tgagatcttt tcctgtccac tgaaatgcct gagcagtagc agtatttcag taaacacgac     480
aatgctgaga atatcaccaa attctccaga cttgctgaag tgttcctttg ggatcctggt     540
tcccaaaaag tatggacata ggtccctgct gtggccccca ggttccaggc catcagtaag     600
gttgggggct gcagactgga ccactgcacc gtggagcaga ggtgaagaaa ccaagacgca     660
gagaggccaa gccccttgcc ttgggtcaca cagccaaagg aggcagagcc agaactcaca     720
accagatcca gaggcaacag ggac atg gcc acc tgg gac gaa aag gca gtc        771
                           Met Ala Thr Trp Asp Glu Lys Ala Val
                           1               5 acc cgc agg gcc aag gtg gct ccc gct gag agg atg agc aag ttc tta      819
Thr Arg Arg Ala Lys Val Ala Pro Ala Glu Arg Met Ser Lys Phe Leu
10              15                  20                  25 agg cac ttc acg gtc gtg gga gac gac tac cat gcc tgg aac atc aac      867
Arg His Phe Thr Val Val Gly Asp Asp Tyr His Ala Trp Asn Ile Asn
            30                  35                  40 tac aag aaa tgg gag aat gaa gag gag gag gag gag gag cag cca          915
Tyr Lys Lys Trp Glu Asn Glu Glu Glu Glu Glu Glu Glu Gln Pro
        45                  50                  55 cca ccc aca cca gtc tca ggc gag gtc atc atc atc tgc ttg gtg gtt      963
Pro Pro Thr Pro Val Ser Gly Glu Val Ile Ile Ile Cys Leu Val Val
    60                  65                  70 ctg gat gcc ctc ctg gtg ctt gct gag ctc atc ctg gac ctg aag atc     1011
Leu Asp Ala Leu Leu Val Leu Ala Glu Leu Ile Leu Asp Leu Lys Ile
75                  80                  85 atc cag ccc gac aag aat aac tat gct gcc atg gta ttc cac tac atg     1059
Ile Gln Pro Asp Lys Asn Asn Tyr Ala Ala Met Val Phe His Tyr Met
90                  95                  100                 105 agc atc acc atc ttg gtc ttt ttt atg atg gag atc atc ttt aaa tta     1107
Ser Ile Thr Ile Leu Val Phe Phe Met Met Glu Ile Ile Phe Lys Leu
            110                 115                 120 ttt gtc ttc cgc ctg gag ttc ttt cac cac aag ttt gag atc ctg gat     1155
Phe Val Phe Arg Leu Glu Phe Phe His His Lys Phe Glu Ile Leu Asp
        125                 130                 135 gcc gtc gtg gtg gtg gtc tca ttc atc ctc gac att gtc ctc ctg ttc     1203
Ala Val Val Val Val Val Ser Phe Ile Leu Asp Ile Val Leu Leu Phe
    140                 145                 150 cag gag cac cag ttt gag gct ctg ggc ctg ctg att ctg ctc cgg ctg     1251
Gln Glu His Gln Phe Glu Ala Leu Gly Leu Leu Ile Leu Leu Arg Leu
155                 160                 165 tgg cgg gtg gcc cgg atc atc aat ggg att atc atc tca gtt aag aca     1299
Trp Arg Val Ala Arg Ile Ile Asn Gly Ile Ile Ile Ser Val Lys Thr
170                 175                 180                 185 cgt tca gaa cgg caa ctc tta agg tta aaa cag atg aat gta caa ttg     1347
Arg Ser Glu Arg Gln Leu Leu Arg Leu Lys Gln Met Asn Val Gln Leu
            190                 195                 200 gcc gcc aag att caa cac ctt gag ttc agc tgc tct gag aag gaa caa     1395
Ala Ala Lys Ile Gln His Leu Glu Phe Ser Cys Ser Glu Lys Glu Gln
        205                 210                 215 gaa att gaa aga ctt aac aaa cta ttg cga cag cat gga ctt ctt ggt     1443
Glu Ile Glu Arg Leu Asn Lys Leu Leu Arg Gln His Gly Leu Leu Gly
    220                 225                 230
```

-continued

```
gaa gtg aac tag acccggacca gctcccctca aaagaagac actgtctcat    1495
Glu Val Asn
    235 gggcctgtgc tgtcacgaga ggaacagctg cccctcctgg gccgcttggt gagaggtttg    1555 gtttgatacc tctgcctccc tcctgccagc atggattctg ggtggacaca gccttgtgga    1615 aggtccagta ccaccaagag ctgcccatcc actcccaccc cacactgtat caaatgtatc    1675 acattttctc atgttgaaca ctttagcctt aattgaaaat gagcaacaaa gctggacaat    1735 tgctagttgt atataaaatt taatctcacc gaatgtacag ttttcaaatt tcacgtgtat    1795 attaaggaac tgatgcatct gagcattctg aagaaagaa aaagaagcta ctttagctgc    1855 cacccccattc tagaaaagtc tcttatttc aagctgttct aaatagcttc gtctcagttt    1915 ccccaaaagg ggtacccagg cccctcctct gtgtgcccca gctgcatcag ccagcttcta    1975 ggtggctcca ttgttttctg ccacctgaca acatttttcc tcaattactg tacaactact    2035 gtataaaata aaacaactac tgtataaaat aaactctctc ttttccctgg aaaaaaaaa    2095 aaaaaaaa    2103
```

<210> SEQ ID NO 4
<211> LENGTH: 236
<212> TYPE: PRT
<213> ORGANISM: Homo sapiens

<400> SEQUENCE: 4

```
Met Ala Thr Trp Asp Glu Lys Ala Val Thr Arg Arg Ala Lys Val Ala
1               5                   10                  15

Pro Ala Glu Arg Met Ser Lys Phe Leu Arg His Phe Thr Val Val Gly
            20                  25                  30

Asp Asp Tyr His Ala Trp Asn Ile Asn Tyr Lys Lys Trp Glu Asn Glu
        35                  40                  45

Glu Glu Glu Glu Glu Glu Gln Pro Pro Thr Pro Val Ser Gly
    50                  55                  60

Glu Val Ile Ile Ile Cys Leu Val Val Leu Asp Ala Leu Leu Val Leu
65                  70                  75                  80

Ala Glu Leu Ile Leu Asp Leu Lys Ile Ile Gln Pro Asp Lys Asn Asn
                85                  90                  95

Tyr Ala Ala Met Val Phe His Tyr Met Ser Ile Thr Ile Leu Val Phe
            100                 105                 110

Phe Met Met Glu Ile Ile Phe Lys Leu Phe Val Phe Arg Leu Glu Phe
        115                 120                 125

Phe His His Lys Phe Glu Ile Leu Asp Ala Val Val Val Val Val Ser
    130                 135                 140

Phe Ile Leu Asp Ile Val Leu Leu Phe Gln Glu His Gln Phe Glu Ala
145                 150                 155                 160

Leu Gly Leu Leu Ile Leu Leu Arg Leu Trp Arg Val Ala Arg Ile Ile
                165                 170                 175

Asn Gly Ile Ile Ile Ser Val Lys Thr Arg Ser Glu Arg Gln Leu Leu
            180                 185                 190

Arg Leu Lys Gln Met Asn Val Gln Leu Ala Ala Lys Ile Gln His Leu
        195                 200                 205

Glu Phe Ser Cys Ser Glu Lys Glu Gln Glu Ile Glu Arg Leu Asn Lys
    210                 215                 220

Leu Leu Arg Gln His Gly Leu Leu Gly Glu Val Asn
225                 230                 235
```